US012191036B2

(12) United States Patent
Park et al.

(10) Patent No.: US 12,191,036 B2
(45) Date of Patent: Jan. 7, 2025

(54) METHOD FOR DISPLAYING ULTRASONIC IMAGE, ULTRASONIC DIAGNOSTIC DEVICE, AND COMPUTER PROGRAM PRODUCT

(71) Applicant: SAMSUNG MEDISON CO., LTD., Hongcheon-gun Gangwon-do (KR)

(72) Inventors: MoonHo Park, Seongnam-si (KR); YeongKyeong Seong, Seongnam-si (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 337 days.

(21) Appl. No.: 17/435,581

(22) PCT Filed: Mar. 12, 2020

(86) PCT No.: PCT/KR2020/003444
§ 371 (c)(1),
(2) Date: Sep. 1, 2021

(87) PCT Pub. No.: WO2020/185003
PCT Pub. Date: Sep. 17, 2020

(65) Prior Publication Data
US 2022/0059227 A1   Feb. 24, 2022

(30) Foreign Application Priority Data

Mar. 12, 2019   (KR) ........................ 10-2019-0028158

(51) Int. Cl.
*A61B 8/08*    (2006.01)
*A61B 8/00*    (2006.01)
(Continued)

(52) U.S. Cl.
CPC ............. *G16H 50/20* (2018.01); *A61B 8/085* (2013.01); *A61B 8/463* (2013.01); *A61B 8/467* (2013.01);
(Continued)

(58) Field of Classification Search
CPC ...................... A61B 8/46–469; A61B 8/085
See application file for complete search history.

(56) References Cited

U.S. PATENT DOCUMENTS 7,615,008 B2    11/2009   Zhang et al.
7,783,094 B2     8/2010   Collins et al.
(Continued)

FOREIGN PATENT DOCUMENTS

CN    102209495 A    10/2011
CN    103455710 A    12/2013
(Continued)

OTHER PUBLICATIONS

Extended European Search Report dated Oct. 31, 2022 issued in European Patent Application No. 20769065.2.
(Continued)

*Primary Examiner* — Carolyn A Pehlke
(74) *Attorney, Agent, or Firm* — MORGAN, LEWIS & BOCKIUS LLP

(57) ABSTRACT

Disclosed is a method for displaying an ultrasonic image, comprising the steps of: identifying a lesion area included in an ultrasonic image; diagnosing the lesion area to obtain a diagnostic result; generating a diagnostic image by displaying, in the lesion area of the ultrasonic image, a first area which is at least one area on which the lesion is diagnosed; and displaying a user interface screen including the diagnostic image and the diagnostic result.

13 Claims, 24 Drawing Sheets

(51) Int. Cl.
| | |
|---|---|
| *G06N 3/08* | (2023.01) |
| *G06T 7/00* | (2017.01) |
| *G06T 7/13* | (2017.01) |
| *G06T 7/70* | (2017.01) |
| *G16H 30/20* | (2018.01) |
| *G16H 50/20* | (2018.01) |

(52) U.S. Cl.
CPC ............. *A61B 8/5223* (2013.01); *G06N 3/08* (2013.01); *G06T 7/0012* (2013.01); *G06T 7/13* (2017.01); *G06T 7/70* (2017.01); *G16H 30/20* (2018.01); *G06T 2207/10132* (2013.01); *G06T 2207/20092* (2013.01); *G06T 2207/30096* (2013.01)

(56) References Cited

U.S. PATENT DOCUMENTS

| | | | |
|---|---|---|---|
| 8,094,896 | B2 | 1/2012 | Dutta et al. |
| 8,625,867 | B2 | 1/2014 | Moriya |
| 8,951,200 | B2 | 2/2015 | Mo et al. |
| 9,468,356 | B2 | 10/2016 | Ikemoto et al. |
| 9,760,689 | B2 | 9/2017 | Chang et al. |
| 9,901,320 | B2 | 2/2018 | DeFreitas et al. |
| 10,265,052 | B2 | 4/2019 | Song |
| 10,349,919 | B2 | 7/2019 | Park et al. |
| 10,383,592 | B2 | 8/2019 | Park |
| 2003/0161513 | A1 | 8/2003 | Drukker et al. |
| 2005/0049497 | A1 | 3/2005 | Krishnan et al. |
| 2006/0120608 | A1 | 6/2006 | Luo et al. |
| 2006/0274928 | A1 | 12/2006 | Collins et al. |
| 2008/0077011 | A1 | 3/2008 | Azuma et al. |
| 2011/0208052 | A1 | 8/2011 | Entrekin |
| 2011/0208061 | A1 | 8/2011 | Chang |
| 2012/0014578 | A1 | 1/2012 | Karssemeijer et al. |
| 2012/0101372 | A1 | 4/2012 | Teramura et al. |
| 2014/0194722 | A1 | 7/2014 | Lee et al. |
| 2014/0348387 | A1 | 11/2014 | Choi et al. |
| 2015/0164481 | A1 | 6/2015 | Lee et al. |
| 2016/0022238 | A1 | 1/2016 | Park |
| 2016/0051220 | A1 | 2/2016 | Lee et al. |
| 2016/0128672 | A1 | 5/2016 | Kim et al. |
| 2017/0172540 | A1 | 6/2017 | Aladahalli et al. |
| 2017/0206653 | A1* | 7/2017 | Shin ................. G06V 10/46 |
| 2017/0262600 | A1 | 9/2017 | Park et al. |

FOREIGN PATENT DOCUMENTS

| | | | |
|---|---|---|---|
| CN | 103823962 | A | 5/2014 |
| CN | 103919573 | A | 7/2014 |
| CN | 104706381 | A | 6/2015 |
| CN | 106466193 | A | 3/2017 |
| CN | 107358015 | A | 11/2017 |
| EP | 2754395 | A1 | 7/2014 |
| JP | 2004-041617 | A | 2/2004 |
| JP | 2005-111258 | A | 4/2005 |
| JP | 2007-524461 | A | 8/2007 |
| JP | 2008-501436 | A | 1/2008 |
| JP | 2010-051554 | A | 3/2010 |
| JP | 2010-082399 | A | 4/2010 |
| JP | 2010-227207 | A | 10/2010 |
| JP | 2011-83590 | A | 4/2011 |
| JP | 2012-157384 | A | 8/2012 |
| JP | 2014-504918 | A | 2/2014 |
| JP | 2014-195729 | A | 10/2014 |
| JP | 6097629 | B2 | 2/2017 |
| KR | 10-2008-0021723 | A | 3/2008 |
| KR | 10-2014-0063288 | A | 5/2014 |
| KR | 10-2014-0138501 | A | 12/2014 |
| KR | 10-2015-0056013 | A | 5/2015 |
| KR | 10-2015-0107515 | A | 9/2015 |
| KR | 10-2016-0012758 | A | 2/2016 |
| KR | 10-2043130 | B1 | 11/2019 |
| KR | 10-2043133 | B1 | 11/2019 |
| KR | 10-2049336 | B1 | 11/2019 |

OTHER PUBLICATIONS

International Search Report and Written Opinion dated Jun. 29, 2020 issued in International Patent Application No. PCT/KR2020/003444 (with English translation).
Chinese Office Action dated Jan. 31, 2024 issued in Chinese Patent Application No. 202080020921.8 (with English translation).
European Communication dated Dec. 18, 2023 issued in European Patent Application No. 20769065.2.
Office Action issued Feb. 27, 2024 for Korean Patent Application No. 10-2019-0028158 (See English Translation).
Chinese Notice of Allowance dated Nov. 4, 2024 issued in Chinese Patent Application No. 202080020921.8 (with English translation).
Chinese Office Action dated Aug. 23, 2024 issued in Chinese Patent Application No. 202080020921.8 (with English translation).
Notice of Allowance issued in corresponding Korean Patent Application No. 10-2019-0028158 dated Nov. 7, 2024, with English translation.
European Notice of Allowance dated Nov. 19, 2024 issued in European Patent Application No. 20769065.2.

* cited by examiner

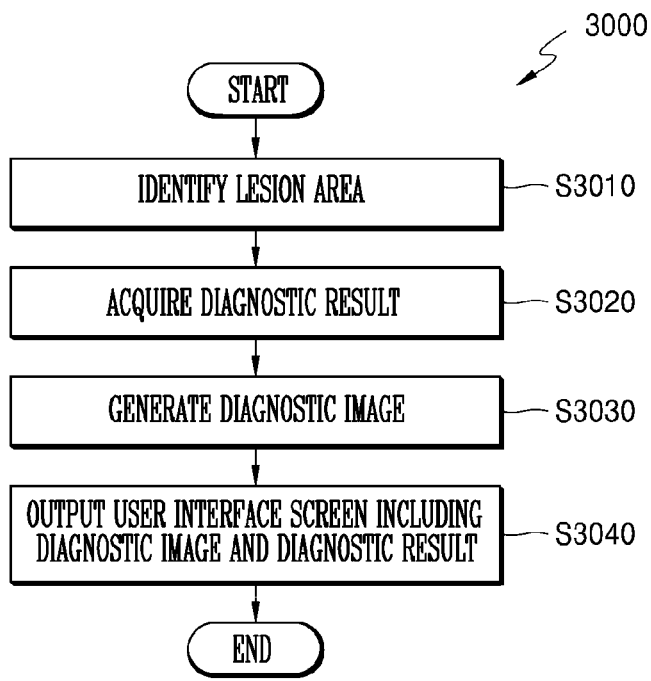
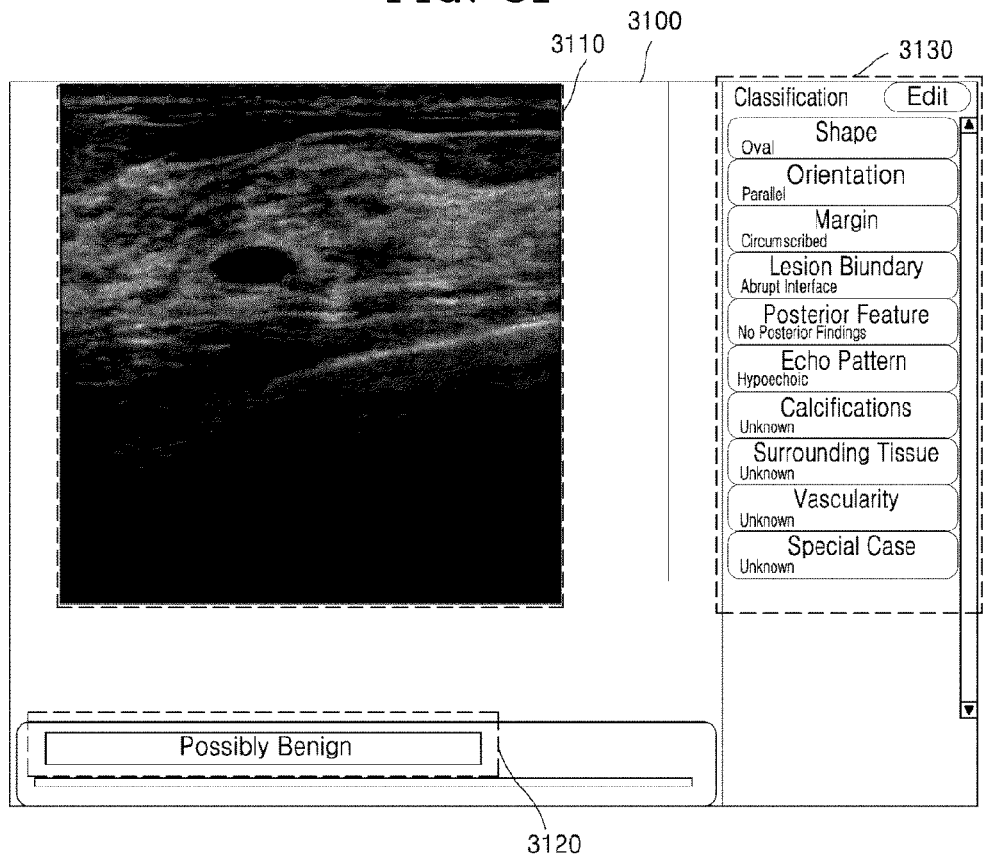

METHOD FOR DISPLAYING ULTRASONIC IMAGE, ULTRASONIC DIAGNOSTIC DEVICE, AND COMPUTER PROGRAM PRODUCT

CROSS-REFERENCE OF RELATED APPLICATIONS

This application is the U.S. National Phase under 35 U.S.C. § 371 of International Patent Application No. PCT/KR2020/003444, filed on Mar. 12, 2020, which in turn claims the benefit of Korean Application No. 10-2019-0028158, filed on Mar. 12, 2019, the entire disclosures of which applications are incorporated by reference herein.

TECHNICAL FIELD

Disclosed embodiments relate to a method of displaying an ultrasonic image, an ultrasound diagnosis device, and a computer program product.

Specifically, the disclosed embodiments relate to a method of displaying an ultrasonic image including a lesion, an ultrasound diagnosis device, and a computer program product.

BACKGROUND ART

Ultrasound diagnosis devices emit ultrasound signals, which are generated from transducers of probes, to an object and receive information of signals reflected from the object to obtain at least one image of a portion (for example, soft tissue or blood) inside the object.

Recently, due to the development of image processing technologies such as a computer aided detection & diagnosis (CAD) system, machine learning, and the like, the ultrasound diagnostic device automatically analyzes an acquired ultrasonic image using a computer to detect an abnormal area that is a portion in which abnormality occurs in an object or to generate an analyzed result. Specifically, the ultrasound diagnosis device may output a user interface screen including a portion in which abnormality occurs in the object and an analyzed diagnostic result (for example, whether the detected portion is a malignant tumor). Accordingly, users (e.g., a doctor and the like) can confirm a diagnostic result corresponding to an abnormal portion detected in a medical image (e.g., an ultrasonic image).

DISCLOSURE

Technical Problem

The disclosed embodiments and effects thereof are directed to providing a method of displaying an ultrasonic image, an ultrasound diagnosis device, and a computer program product, which provide information related to a diagnostic result to allow a user to more accurately diagnose a patient's disease in provision of the diagnostic result by automatically analyzing an ultrasonic image.

Technical Solution

The method of displaying an ultrasonic image according to the disclosed embodiments includes identifying a lesion area included in the ultrasonic image; diagnosing the lesion area to acquire a diagnostic result; displaying a first area in the lesion area, which is at least one area that is the basis of diagnosing the lesion, in the lesion area of the ultrasonic image and generating a diagnostic image; and displaying a user interface screen including the diagnostic image and the diagnostic result.

Advantageous Effects

In accordance with a method of displaying an ultrasonic image, an ultrasound diagnosis device, and a computer program product according to the disclosed embodiments, information related to a diagnostic result is provided so that a user can more accurately diagnose a patient's disease.

Specifically, in accordance with the method of displaying an ultrasonic image, the ultrasound diagnosis device, and the computer program product according to the disclosed embodiments, the user can recognize a portion of the ultrasonic image that is the basis of the diagnostic result so that the user can accurately determine a disease of an object.

Specifically, in accordance with the method of displaying an ultrasonic image, the ultrasound diagnosis device, and the computer program product according to the disclosed embodiments, information related to the diagnostic result acquired on the basis of a computer aided detection & diagnosis (CAD), specifically, a portion of the ultrasonic image that is the basis of the diagnostic result and/or additional information for describing the diagnostic result is provided to the user so that it is possible to assist the user to diagnose a disease through the ultrasonic image.

DESCRIPTION OF DRAWINGS

The present disclosure can be readily understood by the combination of the following detailed description and the accompanying drawings, wherein reference numbers refer to structural elements.

FIG. 30 is a flowchart illustrating a method of displaying an ultrasonic image according to an embodiment.

FIG. 31 is a diagram illustrating an actual implementation example of the user interface screen according to the embodiment.

BEST MODE

Figure 1:
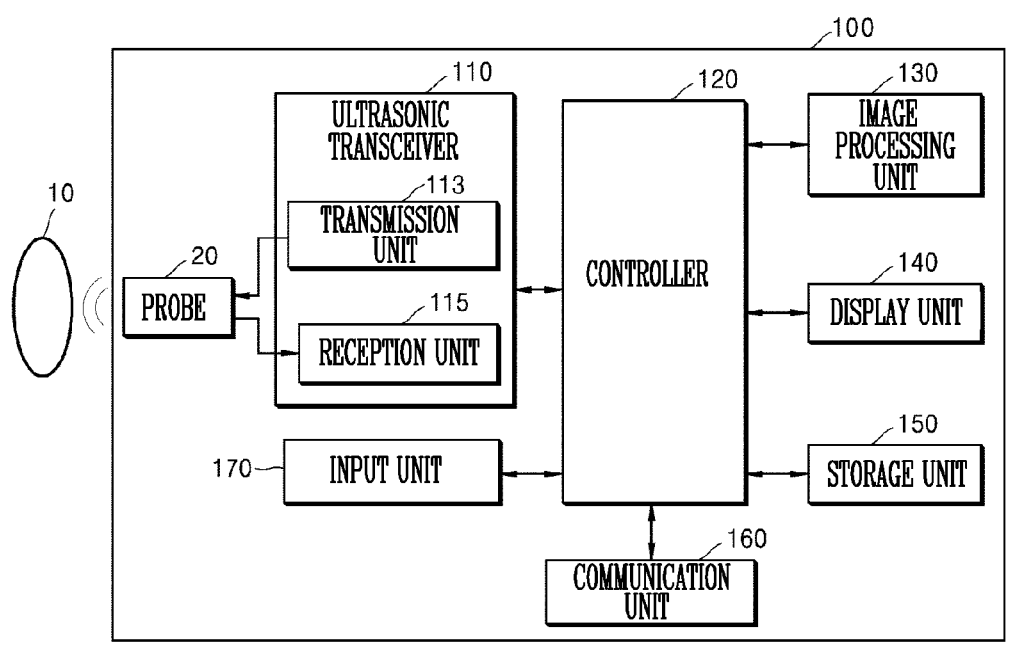
FIG. 1 is a block diagram illustrating a configuration of an ultrasound diagnosis device according to an embodiment.

A method of displaying an ultrasonic image according to disclosed embodiments includes identifying a lesion area included in the ultrasonic image; diagnosing the lesion area to acquire a diagnostic result; displaying a first area in the lesion area, which is at least one area that is the basis of diagnosing a lesion, in the lesion area of the ultrasonic image and generating a diagnostic image; and displaying a user interface screen including the diagnostic image and the diagnostic result.

In addition, when a plurality of features indicating a feature of the lesion in the lesion area are present, the first area may be an area indicating at least one among the plurality of features.

In addition, the first area may be an area that is the basis of determining at least one feature among a shape of the lesion, an orientation of the lesion, a margin of the lesion, an echo with respect to the lesion area, and a posterior of the lesion area.

In addition, the diagnostic result may include information indicating whether the lesion is benign or malignant.

In addition, the generating of the diagnostic image may include, when a plurality of features indicating the lesion area exist, displaying at least one area in the lesion area using at least one among different colors, marks, symbols, transparency, echoes, types of dotted line, and thicknesses of the dotted lines, thereby distinguishing different features from each other among the plurality of features.

In addition, the plurality of features may include at least one among a shape of the lesion, an orientation of the lesion, a margin form of the lesion, an echo with respect to the lesion area, and a posterior feature of the lesion area that are the basis of diagnosing the lesion.

In addition, the generating of the diagnostic image may include, when the feature of the lesion area appearing in a second area included in the lesion area is changed and thus the diagnostic result is changed, displaying the second area in the ultrasonic image and generating the diagnostic image.

In addition, the generating of the diagnostic image may further include displaying the first area to be distinguished from the second area and generating the diagnostic image.

In addition, the displaying of the user interface screen may include displaying the user interface screen including a list including a plurality of items corresponding to a plurality of features indicating the diagnostic image, the diagnostic result, and the lesion.

In addition, the generating of the diagnostic image may further include, in response to a user input for selecting any one among the plurality of items, displaying at least one partial area indicating a feature corresponding to the selected item as the first area in the ultrasonic image and generating the diagnostic image.

In addition, in the list, the plurality of items may include information specifically indicating features corresponding to the plurality of items, and each of the plurality of items may be displayed to match at least one partial area corresponding thereto.

In addition, the displaying of the user interface screen may further include, when a first feature included in the list is changed and thus the diagnostic result is changed, displaying the first feature included in the list to be distinguished from other features.

In addition, the generating of the diagnostic image may include displaying diagnostic information, which is information on the feature of the lesion area appearing in the first area, in the ultrasonic image and generating the diagnostic image.

In addition, acquiring the diagnostic information may include analyzing the ultrasonic image using at least one of a computer aided detection & diagnosis (CAD) technology and an artificial intelligence (AI) technology and acquiring at least one among the lesion area, the diagnostic result, and diagnostic information corresponding to the diagnostic result.

In addition, the identifying of the lesion area may include identifying a contour of the lesion area, and the method of displaying an ultrasonic image may further include, when a plurality of contours exist as the identification result, displaying the plurality of contours in the ultrasonic image and generating a plurality of sub-images; and outputting a user interface screen including the plurality of sub-images.

An ultrasound diagnosis device may include a display; a memory configured to store at least one instruction; and a processor configured to execute at least one of the at least one instruction to identify a lesion area included in an ultrasonic image, diagnose the lesion area to acquire a diagnostic result, display a first area, which is at least one area that is the basis of diagnosing a lesion in the lesion area, in the lesion area of the ultrasonic image to generate a diagnostic image, and control a user interface screen including the diagnostic image and the diagnostic result to be displayed through the display.

A computer program product may include a computer program including commands executable by a computer and configured to be stored in a recording medium to execute a method of displaying an ultrasonic image on a computer, the computer program may include identifying a lesion area included in an ultrasonic image; diagnosing the lesion area to acquire a diagnostic result; displaying a first area in the lesion area, which is at least one area that is the basis of diagnosing a lesion, in the lesion area of the ultrasonic image and generating a diagnostic image; and displaying a user interface screen including the diagnostic image and the diagnostic result.

Modes of the Invention

The present specification describes the principles of the present disclosure and discloses embodiments such that the scope of the present disclosure may be clarified and those skilled in the art to which the present disclosure pertains may implement the present disclosure. The disclosed embodiments may be implemented in various forms.

Like reference numerals refer to like components throughout the present specification. The present specification does not describe all components of embodiments, and a common description in the technical field to which the present disclosure pertains and an overlapping description between the embodiments will be omitted. The term "part" or "portion" used herein may be implemented in software or hardware, and according to embodiments, a plurality of "parts" or "portions" may be implemented as one unit or one element, or one "part" or "portion" may include a plurality of units or elements. Hereinafter, an operation principle and embodiments of the present disclosure will be described with reference to the accompanying drawings.

In the present specification, an "image" may include a medical image obtained by a medical imaging device such as a magnetic resonance imaging (MRI) device, a computed tomography (CT) device, an ultrasound imaging device, and an X-ray imaging device.

In the present specification, an "object" is to be photographed and may include a person, an animal, or a part thereof. For example, the object may include a part (organ) of a human body, a phantom, or the like.

Throughout the specification, an "ultrasonic image" means an image of the object, which is processed based on an ultrasonic signal transmitted to the object and reflected from the object.

Hereinafter, the embodiments will be described in detail with reference to the accompanying drawings.

FIG. 1 is a block diagram illustrating a configuration of an ultrasound diagnosis device according to an embodiment.

FIG. 1 is a block diagram illustrating a configuration of an ultrasound diagnosis device 100 according to an embodiment. The ultrasound diagnosis device 100 may include a probe 20, an ultrasonic transceiver 110, a controller 120, an image processing unit 130, a display unit 140, a storage unit 150, a communication unit 160, and an input unit 170.

The ultrasound diagnosis device 100 may be implemented as a portable type as well as a cart type. Examples of a portable ultrasound diagnosis device may include a smart phone, a laptop computer, a personal digital assistant (PDA), a tablet personal computer (PC), and the like including a probe and an application, but the present disclosure is not limited thereto.

The probe 20 may include a plurality of transducers. The plurality of transducers may transmit ultrasonic signals to an object 10 according to a transmission signal applied from a transmission unit 113. The plurality of transducers may receive ultrasonic signals reflected from the object 10 to form a reception signal. Further, the probe 20 may be implemented integrally with the ultrasound diagnosis device 100 or may be implemented as a separate type in which the probe 20 is connected to the ultrasound diagnosis device 100 in a wired or wireless manner. Further, the ultrasound diagnosis device 100 may include one or more probes 20 according to an implementation form.

The controller 120 controls the transmission unit 113 to form a transmission signal to be applied to each of the plurality of transducers in consideration of the positions and focal points of the plurality of transducers included in the probe 20.

The controller 120 controls a reception unit 115 to convert a reception signal received from the probe 20 in an analog-to-digital conversion manner and to sum the digitally converted reception signal in consideration of the positions and focal points of the plurality of transducers, thereby generating ultrasonic data.

The image processing unit 130 generates an ultrasonic image using the ultrasonic data generated by the ultrasonic reception unit 115.

The display unit 140 may display the generated ultrasonic image and various pieces of information processed by the ultrasound diagnosis device 100. The ultrasound diagnosis device 100 may include one or more display units 140 according to an implementation form. Further, the display unit 140 may be implemented as a touch screen in combination with a touch panel.

The controller 120 may control the overall operation of the ultrasound diagnosis device 100 and a signal flow between internal components of the ultrasound diagnosis device 100. The controller 120 may include a memory that stores a program or data for performing a function of the ultrasound diagnosis device 100 and a processor that processes the program or data. Further, the controller 120 may control the operation of the ultrasonic diagnosis device 100 by receiving a control signal from the input unit 170 or an external device.

The ultrasound diagnosis device 100 may include the communication unit 160 and may be connected, through the communication unit 160, to an external device (for example, a server, a medical device, a portable device (a smart phone, a tablet PC, a wearable device, and the like)).

The communication unit 160 may include one or more components enabling communication with the external device and may include, for example, at least one of a short-range communication module, a wired communication module, and a wireless communication module.

The communication unit 160 may receive a control signal and data from the external device and transmit the received control signal to the controller 120 so that the controller 120 may control the ultrasound diagnosis device 100 in response to the received control signal.

Alternatively, the controller 120 may transmit a control signal to the external device through the communication unit 160 so that the external device may be controlled in response to the control signal of the controller 120.

For example, the external device may process the data of the external device in response to the control signal of the controller received through the communication unit.

A program capable of controlling the ultrasound diagnosis device 100 may be installed in the external device, and the program may include instructions for performing some or all of the operations of the controller 120.

The program may be installed in the external device in advance or may be installed by a user of the external device by downloading the program from a server that provides applications. The server that provides applications may include a recording medium in which the corresponding program is stored.

The storage unit 150 may store various types of data or programs for driving and controlling the ultrasound diagnosis device 100, input/output ultrasonic data, acquired ultrasonic images, and the like.

The input unit 170 may receive a user's input to control the ultrasound diagnosis device 100. For example, the user's input may include an input for manipulating a button, a keypad, a mouse, a trackball, a jog switch, a knob, or the like, an input for touching a touchpad or a touch screen, a voice input, a motion input, and a bioinformation input (e.g., iris recognition or fingerprint recognition), but the present disclosure is not limited thereto.

Figure 2:
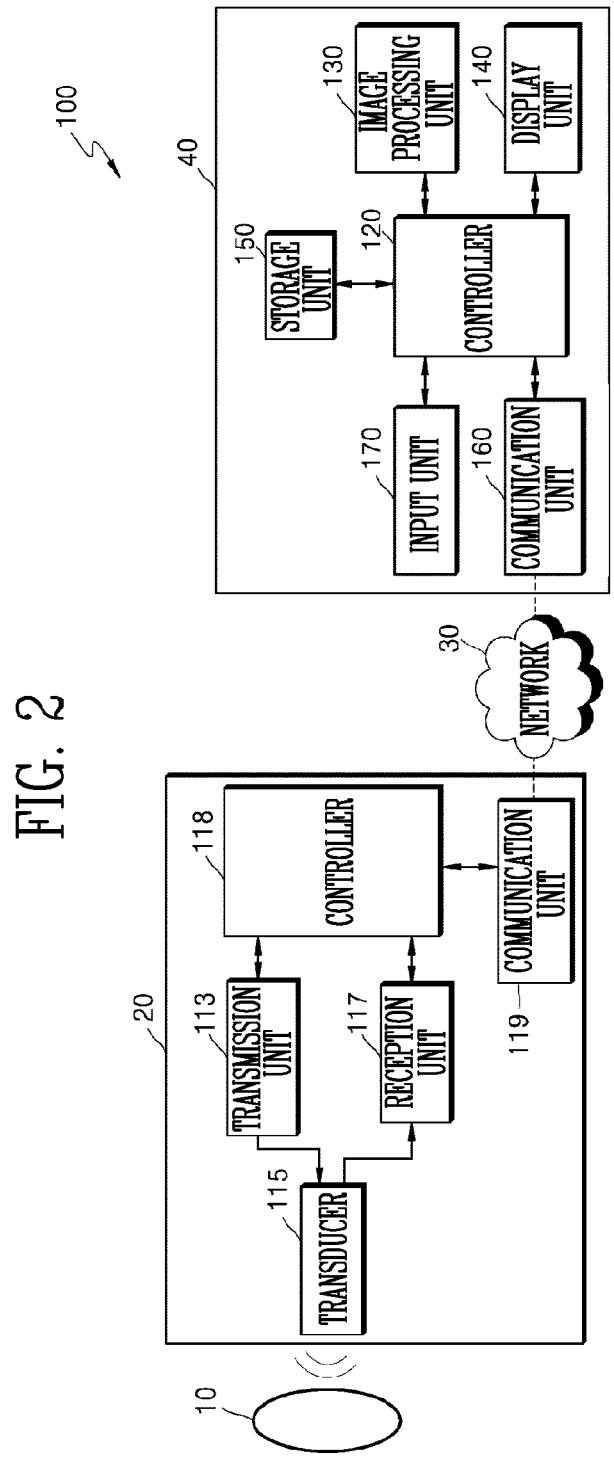
FIG. 2 is a block diagram illustrating a configuration of an ultrasound diagnosis device according to another embodiment.

FIG. 2 is a block diagram illustrating a configuration of an ultrasound diagnosis device according to another embodiment.

Referring to FIG. 2, the ultrasound diagnosis device 100 may include a wireless probe 20 and a main body 40. In FIG. 2, components that are the same as in FIG. 1 are illustrated using the same reference numerals. Therefore, in describing the ultrasound diagnosis device 100 shown in FIG. 2, a description overlapping the description in FIG. 1 will be omitted herein. In addition, since the reception unit 115 may be formed of a plurality of transducers, the "reception unit 115" shown in FIG. 1 is illustrated as a "transducer 115" in FIG. 2.

The wireless probe 20 may include a transmission unit 113, a transducer 115, a reception unit 117, a controller 118, and a communication unit 119. Although the wireless probe 20 has been illustrated as including both of the transmission unit 113 and the reception unit 117 in FIG. 1, according to an implementation form, the wireless probe 20 may include only some of components of the transmission unit 113 and the reception unit 117, and some of the components of the transmission unit 113 and the reception unit 117 may be included in the main body 40. Alternatively, the wireless probe 20 may further include an image processing unit 130.

The transducer 115 may include a plurality of transducers. The plurality of transducers may transmit ultrasonic signals to the object 10 according to a transmission signal applied from the transmission unit 113. The plurality of transducers may receive ultrasonic signals reflected from the object 10 to form a reception signal.

The controller 118 controls the transmission unit 113 to form the transmission signal to be applied to each of the plurality of transducers in consideration of positions and focal points of the plurality of transducers.

The controller 118 controls the reception unit 117 to convert reception signals received from the transducer 115 in an analog-to-digital conversion manner and sum the digitally converted reception signals in consideration of the positions and the focal points of the plurality of transducers, thereby generating ultrasonic data. Alternatively, when the wireless probe 20 includes the image processing unit 130, an ultrasonic image may be generated using the generated ultrasonic data.

The communication unit 119 may transmit the generated ultrasonic data or ultrasonic image to the main body 40 through a wireless network 30 in a wireless manner. In addition, the communication unit 119 may receive a control signal and data from the main body 40.

Further, the ultrasound system 100 may include one or more wireless probes 20 according to an implementation form.

The main body 40 may receive ultrasonic data or an ultrasonic image from the wireless probe 20. The main body 40 may include a controller 120, an image processing unit 130, a display unit 140, a storage unit 150, a communication unit 160, and an input unit 170.

Figure 3A:
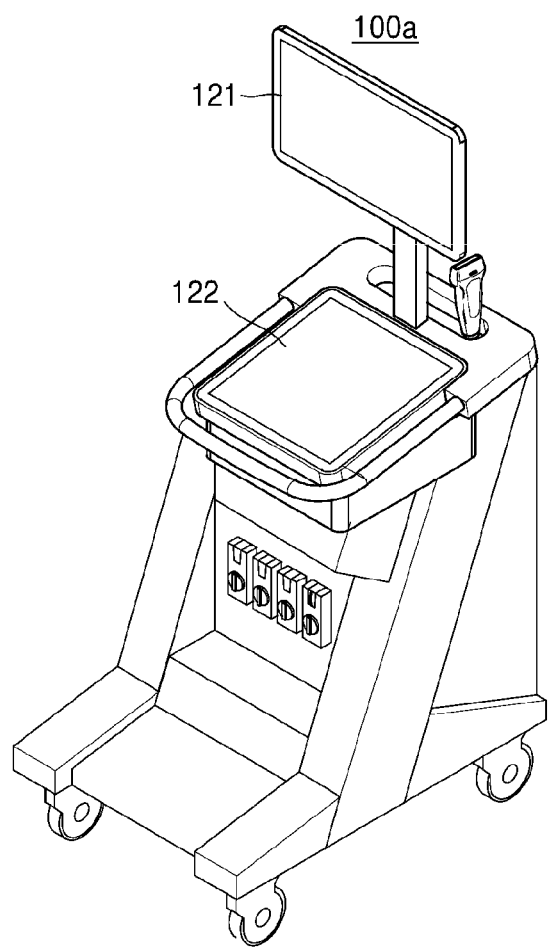
FIG. 3A is a diagram illustrating an appearance of an ultrasound diagnosis device according to an embodiment.

FIG. 3A is a diagram illustrating an appearance of an ultrasound diagnosis device according to an embodiment.

Figure 3B:
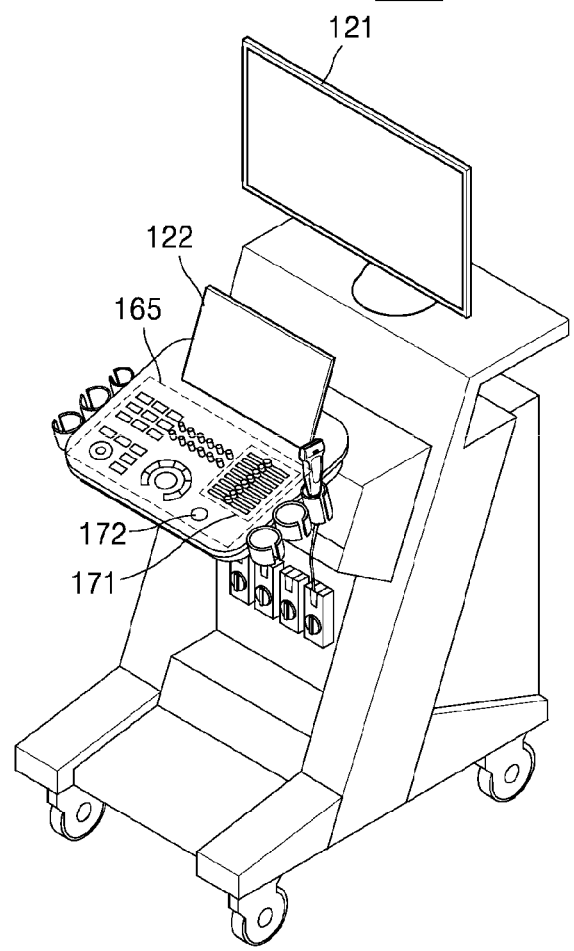
FIG. 3B is another diagram illustrating an appearance of an ultrasound diagnosis device according to an embodiment.

FIG. 3B is another diagram illustrating an appearance of an ultrasound diagnosis device according to an embodiment.

Figure 3C:
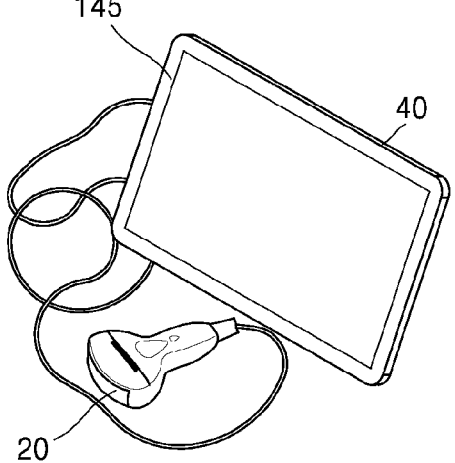
FIG. 3C is another diagram illustrating an appearance of an ultrasound diagnosis device according to an embodiment.

FIG. 3C is another diagram illustrating an appearance of an ultrasound diagnosis device according to an embodiment.

Referring to FIGS. 3A and 3B, ultrasound diagnosis devices 100*a* and 100*b* may each include a main display unit 121 and a sub display unit 122. One of the main display unit 121 and the sub display unit 122 may be implemented as a touch screen. The main display unit 121 and the sub display unit 122 may display the ultrasonic image or various pieces of information processed by the ultrasound diagnosis devices 100*a* and 100*b*. Further, the main display unit 121 and the sub display unit 122 may be implemented as a touch screen and provide a graphical user interface (GUI) to receive data for controlling the ultrasound diagnosis devices 100*a* and 100*b* from a user. For example, the main display unit 121 may display the ultrasonic image, and the sub display unit 122 may display a control panel for controlling the ultrasonic image in the form of the GUI. The sub display unit 122 may receive data for controlling the displaying of the image through the control panel displayed in the form of the GUI. The ultrasound diagnosis devices 100*a* and 100*b* may control, using input control data, the displaying of the ultrasonic image displayed on the main display unit 121.

Referring to FIG. 3B, the ultrasound diagnosis device 100*b* may further include a control panel 165 in addition to the main display unit 121 and the sub display unit 122. The control panel 165 may include a button, a trackball, a jog switch, a knob, and the like, and may receive data for controlling the ultrasound diagnosis device 100*b* from the user. For example, the control panel 165 may include a time gain compensation (TGC) button 171, a freeze button 172, and the like. The TGC button 171 is a button for setting a TGC value for each depth of the ultrasonic image. Further, when detecting the input of the freeze button 172 while scanning the ultrasonic image, the ultrasound diagnosis device 100*b* may maintain a state in which a frame image at a corresponding time point is displayed.

Meanwhile, inputs of the button, the trackball, the jog switch, the knob, and the like included in the control panel 165 may be provided to the GUI in the main display unit 121 or the sub display unit 122.

Referring to FIG. 3C, the ultrasound diagnosis device 100*c* may be implemented as a portable type. Examples of a portable ultrasound diagnosis device 100*c* may include a smart phone, a laptop computer, a PDA, a tablet PC, and the like including a probe and an application, but the present disclosure is not limited thereto.

The ultrasound diagnosis device 100c may include the probe 20 and a main body 40, and the probe 20 may be connected to one side of the main body 40 in a wired or wireless manner. The main body 40 may include a touch screen 145. The touch screen 145 may display the ultrasonic image, various pieces of information processed by the ultrasound diagnosis device, the GUI, and the like.

The method of displaying an ultrasonic image, the ultrasound diagnosis device, and the computer program product according to the disclosed embodiments generate a diagnostic result by analyzing the ultrasonic image to determine whether abnormality occurs in an object and provide information corresponding to the diagnostic result appearing in the ultrasonic image to a user, thereby enabling the user to accurately diagnose a patient's disease by referring to the diagnostic result to increase convenience of the user. Here, the "user" may be a doctor who diagnoses a patient's disease, a sonographer who performs an ultrasound scan on an object of a patient, or the like. In addition, the "information corresponding to the diagnostic result" refers to information displayed on the ultrasonic image corresponding to the diagnostic result, information which is the basis of the diagnostic result, a partial area in the ultrasonic image which is the basis of the diagnostic result, and a partial area in the ultrasonic image which affects the diagnostic result. Hereinafter, for convenience, the "information corresponding to the diagnostic result" will be referred to as "diagnostic information."

As described above, the method of displaying an ultrasonic image, the ultrasound diagnosis device, and the computer program product, which are capable of increasing convenience of a user who automatically receives a diagnostic result will be described in detail with reference to the accompanying drawings.

In the disclosed embodiments, the ultrasound diagnosis device may be an electronic device capable of acquiring, processing, and/or displaying an ultrasonic image. Specifically, specifically, the ultrasound diagnosis device may refer to an electronic device capable of i) identifying a specific portion in the ultrasonic image (e.g., a portion in which a lesion occurs or the like), ii) analyzing the ultrasonic image to acquire a diagnostic result or diagnostic information, or iii) processing, generating, modifying, updating, or displaying a partial image, an entire image, or information used for diagnosis on the basis of the ultrasonic image.

Specifically, as shown in FIGS. 3A to 3C, the ultrasound diagnosis device according to the disclosed embodiments may be implemented as a cart type device as well as a portable type device. Examples of the portable ultrasound diagnosis device may include a picture archiving and communication system (PACS) viewer, a smart phone, a laptop computer, a PDA, a tablet PC, and the like, but the present disclosure is not limited thereto.

Figure 4:
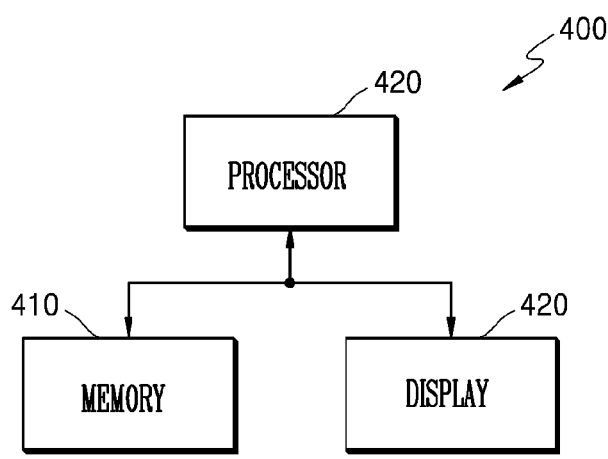
FIG. 4 is a block diagram illustrating a configuration of an ultrasound diagnosis device according to another embodiment.

FIG. 4 is a block diagram illustrating a configuration of an ultrasound diagnosis device according to another embodiment. In FIG. 4, a memory 410, a processor 420, and a display 430 may correspond to the storage unit 150, the controller 120, and the display unit 140 shown in FIG. 1, respectively, and thus a description overlapping the description of FIG. 1 will be omitted herein.

Referring to FIG. 4, an ultrasound diagnosis device 400 according to the disclosed embodiments includes the memory 410, the processor 420, and the display 430.

The memory 410 stores at least one instruction.

The display 430 displays a predetermined screen.

The processor 420 may execute at least one of the at least one instruction stored in the memory 410 to perform a predetermined operation or may control other components in the ultrasound diagnosis device 400 to perform a predetermined operation.

Specifically, the processor 420 executes at least one of the at least one instruction to identify a lesion area included in the ultrasonic image, diagnoses the lesion area to acquire a diagnostic result, displays a first area, which is at least one area that is the basis of diagnosing a lesion in the lesion area, on the lesion area of the ultrasonic image to generate a diagnostic image, and controls a user interface screen including the diagnostic image and the diagnostic result to be displayed through the display.

Here, the lesion refers to a change in the living body caused due to a disease. Specifically, a lesion may refer to all forms in which an object does not have a healthy tissue form or a case in which an object has a different state when compared with a healthy state. Specifically, the lesion may be largely classified into benign and malignant. In addition, a benign lesion may correspond to a tumor, and a malignant lesion may correspond to cancer.

In addition, in the disclosed embodiments, the "lesion area" may be a concept including not only an inner area of the lesion formed by the contour of a lesion, but also an outer area adjacent to the contour of the lesion. That is, the lesion area may mean not only an area in which the lesion itself is imaged in the ultrasonic image, but also an area in which features of the lesion are imaged.

In addition, when the lesion is present in the object, diagnostic information may be information indicating at least one among an identified lesion area, a size of the lesion, a position of the lesion, and features of the lesion (e.g., a metastasis probability, malignant risk, and the like). In addition, the diagnostic information may include standard terms for diseases defined by the society or association. For example, the diagnostic information may include information on a plurality of items included in a lexicon which is a standard term for ultrasound examination defined by the American College of Radiology (ACR).

In addition, the diagnostic result may include information indicating whether the identified lesion is malignant or benign or include a specific name of the lesion. As another example, the diagnostic result may include information indicating whether the identified lesion is a papule, a nodule, a tumor, or cancer. As another example, the diagnostic result may include information indicating a specific name of the lesion (e.g., a breast tumor, breast cancer, a thyroid tumor, a thyroid nodule, thyroid cancer, and the like).

Hereinafter, for convenience of description, a case including information indicating whether a diagnostic result is malignant or benign will be described and illustrated as an example. For example, the diagnostic result may be expressed as "Possibly benign," "Benign," "Possibly malignant," "Malignant," or the like.

In the disclosed embodiments, a first area is at least a part of the lesion area that is the basis of diagnosing the lesion and may refer to at least a part of the ultrasonic image that is the basis of diagnosing the lesion. For example, when a lesion in the object is a malignant lesion, the diagnostic result may be "malignant." In this case, the first area may be a feature in the ultrasonic image, which is the basis of determining the corresponding lesion as malignant, or an area in which the feature in the ultrasonic image is imaged. The first area will be described in detail below with reference to FIGS. 6 to 11.

In addition, in the disclosed embodiments, "at least one among a, b, and c" may have a meaning including all cases of including only a, including only b, including only c, including a and b, including a and c, including b and c, and including a, b, and c.

Specifically, the display 430 displays a predetermined screen under the control of the processor 420. The display 430 may display a medical image (e.g., an ultrasonic image), a user interface screen, information on a patient, history information on a patient's disease, image processing information, and the like. Here, the image processing information may include an intermediate product or a final product which is generated by processing the ultrasonic image by the processor 420. In addition, the "image processing" may refer to an operation of processing, generating, modifying, and/or updating an ultrasonic image.

For example, the display 430 may display a user interface screen including at least one among an ultrasonic image, a diagnostic image corresponding to the ultrasonic image, a diagnostic result for a lesion identified on the basis of the ultrasonic image, and information for describing the diagnostic result.

Specifically, the memory 410 may store at least one program required for an operation of the ultrasound diagnosis device 400 or at least one instruction required for executing the at least one program. In addition, the memory 410 may include at least one processor for performing the above-described operations.

In addition, the memory 410 may store at least one among an ultrasonic image, information related to the ultrasonic image, information on a patient, information on an object, and information on a testee. In addition, the memory 410 may store at least one among information and an image which are generated by the processor 420. In addition, the memory 410 may store at least one among an image, data, and information which are received from an external electronic device (not shown).

The processor 420 may generally control an operation of the ultrasound diagnosis device 400. Specifically, the processor 420 may execute at least one instruction to perform a predetermined operation or control the predetermined operation to be performed. Here, the instruction executed by the processor 420 may be at least one of the at least one instruction stored in the memory 410.

In addition, the processor 420 may be implemented in the form of one processor or in the form in which a plurality of processors are combined.

In addition, the processor 420 may include an internal memory (not shown) and at least one processor (not shown) for executing at least one stored program. Specifically, the internal memory (not shown) of the processor 420 may store one or more instructions. In addition, the at least one processor (not shown) included in the processor 420 may execute at least one among the one or more instructions stored in the internal memory (not shown) of the processor 420 to perform a predetermined operation.

Specifically, the processor 420 may include a random access memory (RAM) (not shown) used as a storage area for storing signals or data which are input from the outside of the ultrasound diagnosis device 400 or used as a storage area corresponding to various tasks performed by the ultrasound diagnosis device 400, a read only memory (ROM) (not shown) in which a control program and/or a plurality of instructions for controlling the ultrasound diagnosis device 400 are stored, and at least one processor (not shown). The processor (not shown) may include a graphic processor (Graphic Processing Unit, not shown) for graphics processing corresponding to video data. The processor (not shown) may be implemented as a system on chip (SoC) in which a core (not shown) and the GPU (not shown) are integrated. A processor (not shown) may include a single core, a dual core, a triple core, a quad core, and multiple cores thereof.

For convenience of description, in the disclosed embodiment, a case in which the processor 420 executes an instruction stored in the memory 410 to perform or control a predetermined operation will be described as an example.

Figure 5:
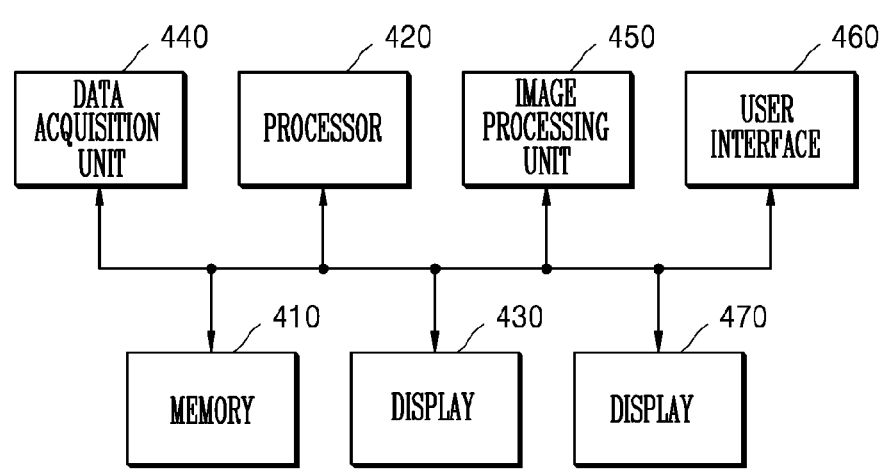
FIG. 5 is a block diagram illustrating a configuration of an ultrasound diagnosis device according to another embodiment.

FIG. 5 is a block diagram illustrating a configuration of an ultrasound diagnosis device according to another embodiment. In FIG. 5, components that are the same as in FIG. 4 are illustrated using the same reference numerals. Therefore, in describing an ultrasound diagnosis device 500 shown in FIG. 5, a description overlapping the description in FIG. 4 will be omitted herein.

When compared with the ultrasound diagnosis device 400, the ultrasound diagnosis device 500 may further include at least one among a data acquisition unit 440, an image processing unit 450, a user interface 460, and a communication unit 470. The data acquisition unit 440, the image processing unit 450, the user interface 460, and the communication unit 470 may be identically correspond to the ultrasonic transceiver 110, the image processing unit 130, the input unit 170, and the communication unit 160 of FIG. 1, respectively. Therefore, in describing the ultrasound diagnosis device 500, a description overlapping the description in FIG. 1 will be omitted herein.

The data acquisition unit 440 may acquire ultrasonic data. Specifically, the data acquisition unit 440 may receive an ultrasound echo signal, which is reflected from the object, through the probe 20 under the control of the processor 420.

Specifically, the data acquisition unit 440 may directly acquire raw data for generating an ultrasonic image under the control of the processor 420. In this case, the data acquisition unit 440 may correspond to the ultrasonic transceiver 110. Here, the raw data may refer to original data corresponding to the ultrasound echo signal acquired by being reflected from the object or refer to data before processing.

Then, the processor 420 may control to generate an ultrasonic image corresponding to the ultrasonic echo signal received through the data acquisition unit 440. Specifically, the processor 420 may control the image processing unit 450 to generate the ultrasonic image using the ultrasound echo signal.

In addition, the data acquisition unit 440 may receive an ultrasonic image from an external electronic device (not shown), such as an external ultrasound diagnosis device (not shown), under the control of the processor 420. Specifically, the data acquisition unit 440 may be connected to an external electronic device (not shown) through a wired/wireless communication network and may receive the ultrasonic image or raw data for generating the ultrasonic image, which are transmitted from the external electronic device (not shown) under the control of the processor 420. When the data acquisition unit 440 acquires the raw data, the processor 420 may control the image processing unit 450 to generate the ultrasonic image using the raw data received through the data acquisition unit 440.

When the data acquisition unit 440 receives the ultrasonic image or the raw data from the external electronic device (not shown), the data acquisition unit 440 may include the communication unit 470. That is, the communication unit 470 may be the data acquisition unit 440 itself, and the communication unit 470 may be implemented in the form of being included in the data acquisition unit 440.

The image processing unit 450 may perform at least one operation of generating an ultrasonic image and processing the ultrasonic image. In addition, the image processing unit 450 may be implemented in the form of being included in the processor 420.

For example, when the processor 420 includes a plurality of processors, any one among the plurality of processors included in the processor 420 may be an image processor for image processing.

The user interface 460 may receive predetermined data or a predetermined command from a user. The user interface 460 may correspond to the input unit 170 of FIG. 1. In addition, the user interface 460 may be formed as a touch screen or a touch pad which is integrally formed with the display 430. As another example, the user interface 460 may include a user input device such as a button, a key pad, a mouse, a trackball, a jog switch, and a knob. In addition, the user interface 460 may include a microphone, a motion detection sensor, and a biometric information detection sensor for receiving a voice input, a motion input, and a biometric information input (e.g., iris recognition, fingerprint recognition, and the like).

Thus, the user interface 460 may receive inputs manipulating buttons, keyboards, mouses, trackballs, jog switches, and knobs, an input of touching a touch pad or a touch screen, a voice input, a motion input, and/or a biometric information input (e.g., iris recognition, fingerprint recognition, and the like).

In the disclosed embodiment, the processor 420 may identify the lesion area on the basis of a user input received through the user interface 460. For example, the ultrasound diagnosis device 500 may display the ultrasonic image through the display 430. The user may look at the ultrasonic image and input an input for selecting a predetermined position or a predetermined area corresponding to a portion suspected of a lesion in the ultrasonic image through the user interface 460. Then, on the basis of the received user input, the processor 420 may analyze the ultrasonic image around or near the predetermined position or the predetermined area selected by the user input or analyze the ultrasonic image within a predetermined range based on the selected position or the predetermined area. Thus, according to the analysis result, it is possible to identify a contour of the lesion and the lesion area formed by the contour of the lesion.

In addition, in the disclosed embodiment, the processor 420 may automatically detect the lesion area included in the ultrasonic image through a computer-based image processing technology. In the above-described example, the user may look at the ultrasonic image and input an input for selecting a predetermined position or a predetermined area corresponding to a portion suspected of a lesion in the ultrasonic image through the user interface 460. Then, the processor 420 may analyze at least a partial area of the ultrasonic image corresponding to a position or an area selected through the user input using a computer-based automatic diagnosis technology. In addition, as the analysis result, the processor 420 may precisely extract the margin of the lesion or the lesion area formed by the margin of the lesion.

Here, the computer-based image processing technology may include a diagnosis technology based on machine learning, and the like.

Here, the machine learning may be performed through a CAD system which determines and detects whether abnormality or a lesion occurs in an object through a computer operation, a statistical machine learning based on data, or an artificial intelligence system which performs machine learning according to an artificial intelligence technology. In the disclosed embodiment, the processor 420 may analyze the ultrasonic image using a computer-based image processing technology and acquire desired information (e.g., the lesion area, information on the lesion, a diagnostic result, and the like) as the analysis result.

Here, unlike the existing rule-based smart system, the artificial intelligence (AI) system is a system in which a machine learns and determines by itself and generates a result desired by the user. The AI technology includes machine learning (deep learning) and element technologies using the machine learning. The machine learning is an algorithm technology which categorizes/learns features of input data by itself, and the element technology is a technology which utilizes a machine learning algorithm such as deep learning and includes technical fields such as linguistic understanding, visual understanding, deduction/prediction, knowledge expression, and motion control.

In the disclosed embodiment, the processor 420 may use the machine learning that is the aforementioned computer-based image processing technology in identifying the lesion area, acquiring the diagnostic result, acquiring the diagnostic information, and/or establishing a criterion for identifying the lesion.

Specifically, image processing through the AI technology may be performed through an operation based on a neural network. Specifically, an operation based on a neural network such as a deep neural network (DNN) may be used. In addition, an operation of the DNN may include an operation of a convolutional neural network (CNN). An operation of processing the ultrasonic image through an AI technology will be described in detail below with reference to FIG. 29.

Hereinafter, operations performed in the ultrasound diagnosis device 100, 400, or 500 according to the disclosed embodiment will be described in detail with reference to FIGS. 6 to 32. In addition, for convenience of description, the operations of the disclosed embodiment will be described below using the ultrasound diagnosis device 400 of FIG. 4 as an example.

Figure 6:
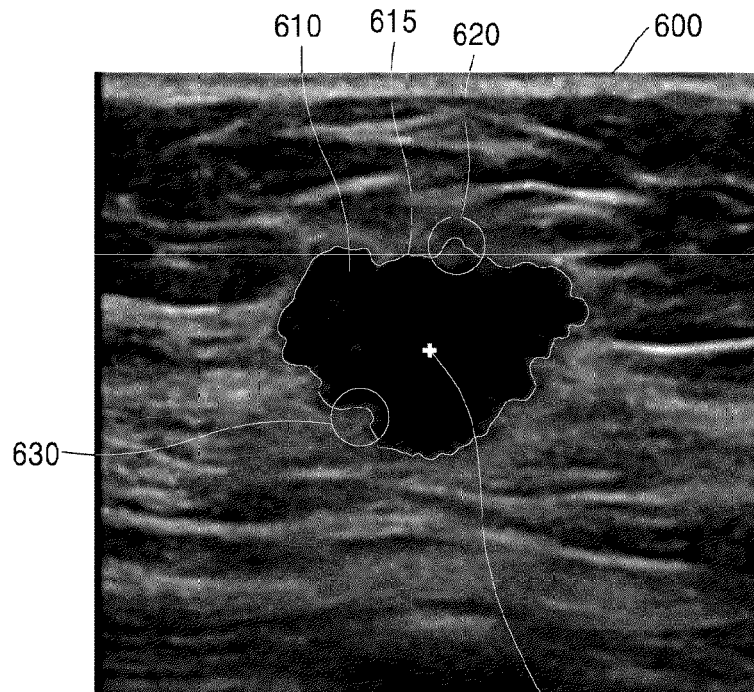
FIG. 6 is a diagram illustrating an ultrasonic image obtained in an embodiment.

FIG. 6 is a diagram illustrating an ultrasonic image obtained in an embodiment.

Referring to FIG. 6, an ultrasonic image 600 acquired by the ultrasound diagnosis device 400 is shown. Specifically, FIG. 6 illustrates the ultrasonic image 600 corresponding to a breast portion acquired through a breast ultrasound scan as an example.

The processor 420 identifies a lesion area 610 included in the ultrasonic image 600. Specifically, the processor 420 may analyze the ultrasonic image 600 using an automatic diagnosis technology such as a CAD technology or an AI technology. In addition, as the analysis result, the processor 420 may automatically detect the lesion area 610 included in the ultrasonic image 600. Hereinafter, operations of identifying the lesion area 610 and analyzing the lesion area 610 to acquire at least one of a diagnostic result and diagnostic information may be performed using a CAD technology.

For example, the user may look at the ultrasonic image 600 and select an area suspected of the lesion or one position or a predetermined area in an area adjacent to a suspected portion in the ultrasonic image 600 through a user interface 460. Specifically, the user may point, touch, or click on one position 611 in the lesion area 610 through the user interface 360. Then, the processor 420 may analyze an area surrounding the position or area selected through the user input using a CAD technology or an AI technology to accurately detect the lesion area 610.

In addition, the processor 420 may analyze the lesion area 610 using a CAD technology or an AI technology to acquire a diagnostic result.

In addition, in order to allow the user to easily recognize the detected lesion area 610, the processor 420 may process a contour 615 of the lesion area 610 to generate a diagnostic image (not shown) so as to allow the contour 615 of the lesion area 610 to be clearly displayed. For example, in order to allow the user to easily recognize the contour 615 of the lesion area 610, the diagnostic image (not shown) may be an image which is generated by marking a line of a predetermined color on the contour 615 of the lesion area 610 in the ultrasonic image 600. In addition, various processes of allowing the user to easily recognize the lesion area 610 may exist. As another example, the diagnostic image (not shown) may be generated through a process of adjusting transparency of the lesion area 610, marking the lesion area 610 with a specific color or pattern, or marking the contour 615 of the lesion area 610 with an outline such as a dotted line or a solid line.

Then, the processor 420 displays a first area on the lesion area 610 of the ultrasonic image 600 to generate the diagnostic image (not shown). Here, the first area is at least a part of the lesion area that is the basis of diagnosing the lesion and may refer to at least a part of the ultrasonic image that is the basis of diagnosing the lesion.

When the lesion is distinguished as malignant or benign, a feature of the lesion classified as malignant is different from a feature of the lesion classified as benign. When the lesion is distinguished as malignant or benign, a criterion for distinguishing the lesion may be set on the basis of at least one among a CAD system, an AI system, and a user setting. Various types of lesions exist, and the lesions may be distinguished according to various criteria. Thus, the lesion discrimination criterion may be optimized and set by an experiment or machine learning.

Specifically, the lesion area 610 is the basis of analyzing the lesion, and the diagnostic result may be determined according to contents contained in a periphery of the lesion area 610 and an inner area thereof. For example, the lesion may be distinguished as a specific lesion on the basis of a result of analyzing at least one among a shape of the lesion area, an orientation of the lesion, a margin of the lesion, an echo feature exhibiting in the lesion area, and a posterior feature of the lesion area.

In diagnosing the lesion using a CAD technology and the like, it is important to accurately extract the lesion area. In addition, the lesion area may be accurately extracted only when image accuracy of the lesion area 610, which is an area in which the lesion is imaged in the ultrasonic image 600, and image accuracy of a surrounding area of the lesion area 610 are high.

However, according to a specific shape of the lesion, quality of the ultrasonic image, the product specifications of the ultrasound diagnosis device which performs an ultrasound scan, and a setting applied during the ultrasound scan of the ultrasound diagnosis device, there may occur a case in which an accurate extraction of the lesion area is difficult.

In particular, when the contour of the identified lesion area is changed, the shape of the lesion area, the orientation of the lesion, the margin feature of the lesion, and the like may be changed. Accordingly, the diagnostic result of the lesion may also be varied. Therefore, when the lesion area is not accurately extracted and thus the diagnostic result is not accurately derived, reliability of the diagnostic result may be degraded.

The existing ultrasound diagnosis device, which provides a diagnostic result using a CAD system and the like, provides only a diagnostic result without describing a process of deriving the diagnostic result. Accordingly, even when there occurs a case in which an erroneous diagnostic result is provided or a case in which determination is ambiguous in deriving the diagnostic result, the user does not recognize such errors. Thus, when the user trusts the erroneous diagnostic result to finally derive the diagnostic result, a patient's disease may be misdiagnosed.

In addition, the provision of the erroneous diagnostic result does not particularly help the user in diagnosing the object and may confuse the user in diagnosing the object.

In the embodiments of the present disclosure, in the ultrasound diagnosis device 400 which identifies a lesion area by analyzing an ultrasonic image and provides a diagnostic result for the lesion, the diagnostic image in which an area (specifically, the first area) that is the basis of the diagnostic result is displayed is provided to the user, thereby allowing the user to trust the diagnostic result more and to more easily diagnose the object by referring to the diagnostic result and the first area.

For example, when a shape of the lesion area has an irregular or variable shape, a margin of the lesion area becomes a spiculated pattern, and an echo feature has a low-level marked hyperechogenic feature, a breast lesion is more likely to be diagnosed as malignant. Since the lesion area 610 included in the ultrasonic image 600 shown in FIG. 6 has the above-described feature of the malignant lesion, the processor 420 may generate a diagnostic result such as "Malignant" or "Possibly Malignant" as the analysis result of the lesion area 610 of the ultrasonic image 600.

In the above-described example, the basis of diagnosing the lesion included in the ultrasonic image 600 as malignant may be that the shape of the lesion area 610 has an irregular shape instead of an oval or an ellipsoid and a spiculated pattern is present in the margin of the lesion area. Accordingly, the shape of the contour 615 of the lesion area 610 and margin areas 620 and 630, each having a spiculated pattern in the lesion area 610, may be the basis of the diagnostic result (specifically, the lesion is benign).

Therefore, in the disclosed embodiment, since the diagnostic image, in which the areas that are the basis for diagnosing the lesion area 610 as malignant (e.g., 620, 615 which is an area in which a contour is displayed, or 630) are displayed, is provided to the user, the user may diagnose the object quickly and easily.

In the embodiments of the present disclosure, the first area, which is at least one area that is the basis of diagnosing the lesion, may be displayed to be distinguished from other area in the diagnostic image. Specifically, the processor 420 may distinguish and display the first area and other areas in the diagnostic image using at least one among a specific color, a symbol, transparency, an echo, a mark, and a line having a specific pattern.

Figure 7:
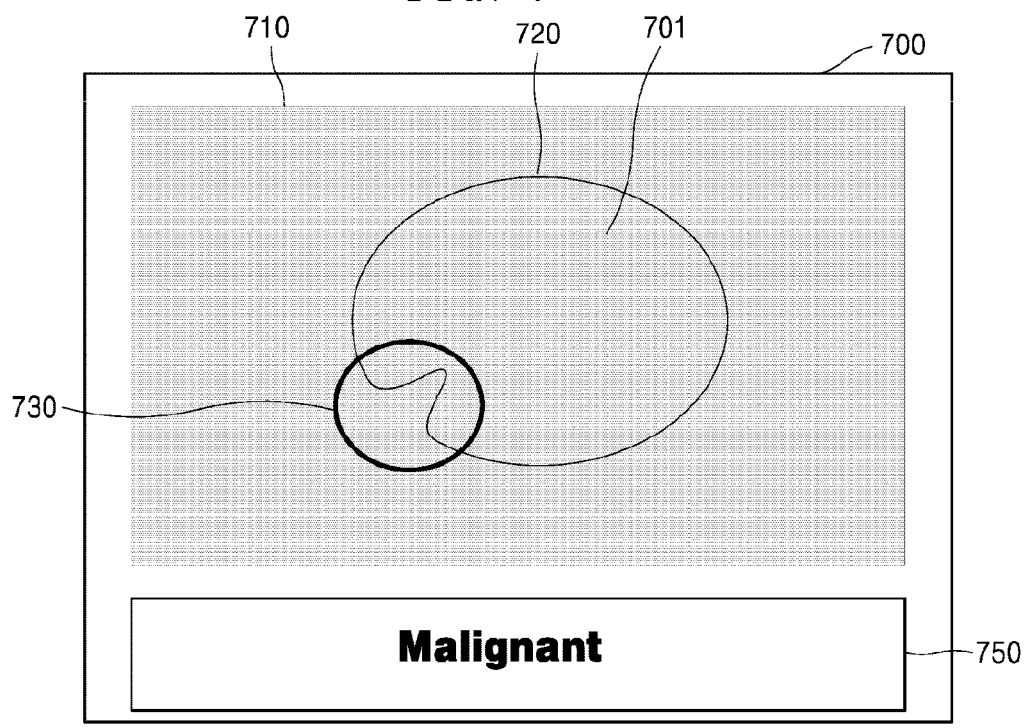
FIG. 7 is a diagram illustrating a user interface screen including a diagnostic image provided in an embodiment.

FIG. 7 is a diagram illustrating a user interface screen including a diagnostic image provided in an embodiment. Specifically, FIG. 7 illustrates a user interface screen 700 output from the ultrasound diagnosis device 400. For convenience of description, in FIGS. 8, 10–21, and 23 to 28 including FIG. 7, a lesion area (e.g., 720) included in a diagnostic image (e.g., 710) is simplified and schematically illustrated. Here, a contour of the lesion area 720 may correspond to the contour 615 of the lesion area of FIG. 6 identically.

Referring to FIG. 7, the user interface screen 700 may include the diagnostic image 710 and a partial screen 750 indicating a diagnostic result. Hereinafter, for convenience of description, the partial screen 750 indicating the diagnostic result included in the user interface screen 700 will be referred to as a "diagnostic result 750."

Referring to FIG. 7, a portion that is the basis of determining a lesion imaged in the diagnostic image 710 as "Malignant" may be referred to as a portion having a spiculated pattern of the margin of the lesion area 720. Accordingly, the diagnostic image 710 may be an image in which an area 730 having a spiculated pattern is displayed as a first area in the margin of the lesion area 720.

For example, the processor 420 may display the first area (e.g., 730) to be distinguished from other areas. In FIG. 7, a case in which the first area is displayed using an area indication line is illustrated as an example. Accordingly, the user may look at the diagnostic image 710, which is an ultrasonic image including the lesion, to easily recognize a feature of the lesion (specifically, a margin having a spiculated pattern) imaged in the first area (e.g., 730). Thus, the user may quickly and easily determine whether the diagnostic result (e.g., "Malignant") provided by the ultrasound diagnosis device is correct.

In addition, in FIG. 7, a case in which one area is displayed as the first area in the diagnostic image 710 is illustrated as an example. However, in the disclosed embodiment, the first area may be present as a plurality of areas in the diagnostic image 710. That is, in the disclosed embodiment, the "first area" merely refers to the area that is the basis of diagnosing the lesion and does not refer to the number of area being one.

In addition, when a plurality of features indicating a feature of the lesion exist in the lesion area (e.g., 610 or 701), the first area may be an area indicating at least one among the plurality of features. Here, the plurality of features are features of the lesion for distinguishing a type of a lesion and include the above-described shape of the lesion area, the orientation of the lesion, the margin of the lesion, the echo feature appearing in the lesion area, and a posterior feature of the lesion area.

Specifically, the plurality of above-described features may correspond to a plurality of items included in a lexicon which is a standard term for ultrasound examination defined by the ACR.

Accordingly, the first area may be an area indicating at least one feature among the plurality of above-described features.

Specifically, in FIG. 6, the displayed first areas 620 and 630 may be areas indicating the margin of the lesion among the above-described features. In addition, in FIG. 6, the displayed contour line 615 may be an area indicating the shape of the lesion area among the above-described features.

In the disclosed embodiment, in the diagnostic image 710, at least one area indicating any one among the plurality of above-described features may be displayed as the first area.

In addition, in the diagnostic image 710, a plurality of areas indicating two or more of the plurality of above-described features may be displayed as the first area. Here, when the plurality of areas indicating the plurality of features are displayed in the diagnostic image 710, the plurality of areas may be displayed in the diagnostic image 710 to allow different features to be distinguished and displayed. Specifically, when the plurality of features indicating the lesion area exist, the processor 420 may display at least one area in the lesion area using at least one among different colors, marks, symbols, transparency, echo, a type of dotted line, and a thickness of the dotted line, thereby distinguishing different features from each other among the plurality of features. In addition, the processor 420 may control the diagnostic image in which the at least one area is displayed to be displayed.

For example, when the ultrasonic image 600 shown in FIG. 6 is generated as a diagnostic image, the areas 620 and 630 which are areas indicating the margin feature of the lesion may be marked with an indication line having a red color, and the contour line 615 indicating the shape feature of the lesion may be marked with an indication line having a blue color.

Figure 8:
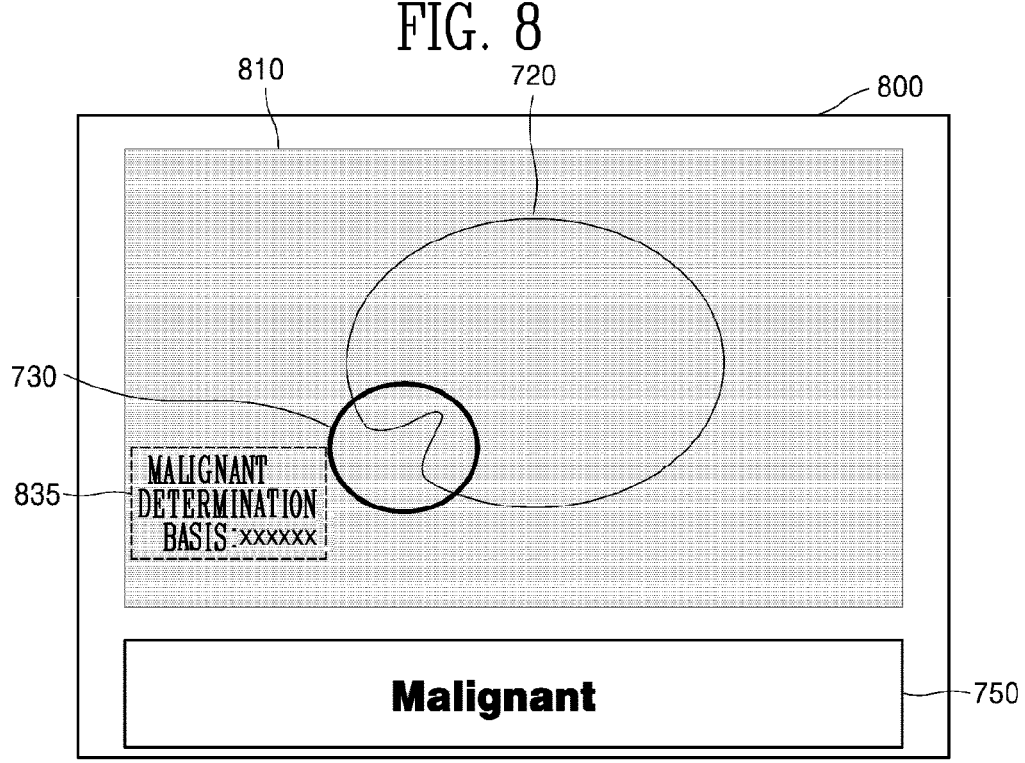
FIG. 8 is a diagram illustrating a user interface screen including another diagnostic image provided in an embodiment.

FIG. 8 is a diagram illustrating a user interface screen including another diagnostic image provided in an embodiment. Specifically, FIG. 8 illustrates a user interface screen 700 output from the ultrasound diagnosis device 400. In the user interface screen 800 shown in FIG. 8, the same components as in the user interface screen 700 shown in FIG. 7 are illustrated using the same reference numerals.

In the disclosed embodiment, the processor 420 may display diagnostic information, which is information on the feature of the lesion area (e.g., the margin feature of the lesion area) appearing in the first area (e.g., 730), in the ultrasonic image, thereby generating a diagnostic image 810.

Here, the diagnostic information may be information indicating the feature of the lesion area appearing in the first area or information that is the basis of deriving a diagnostic result.

For example, since the feature of the lesion area appearing in the first area 730 becomes the margin feature of the lesion area, diagnostic information 835 may be "Margin: spiculated" which is information specifically indicating the margin feature. In addition, the diagnostic information may be "malignant determination basis: Margin-spiculated" which is information that is the basis of deriving malignant determination that is the diagnostic result.

In addition, the diagnostic information may be displayed in an area corresponding to the first area in the diagnostic image (e.g., an area adjacent to the first area that does not interfere with user's observation of the first area).

In the above-described example, the processor 420 may generate the diagnostic image 810 by displaying "Margin: spiculated" or "malignant determination basis: Margin—spiculated" in the area 835 adjacent to the first area 730.

Figure 9:
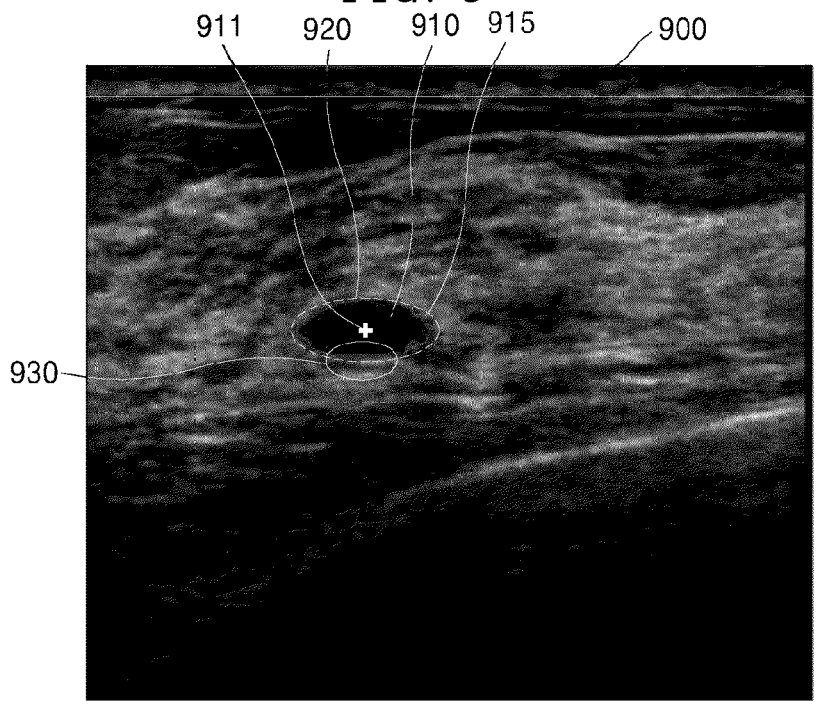
FIG. 9 is another diagram illustrating an ultrasonic image obtained in an embodiment.

FIG. 9 is another diagram illustrating an ultrasonic image obtained in an embodiment. Referring to FIG. 9, an ultrasonic image 900 acquired by the ultrasound diagnosis device 400 is shown. Specifically, FIG. 9 illustrates the ultrasonic image 900 corresponding to a breast portion acquired through a breast ultrasound scan as an example.

In the case of a breast lesion, a shape of a lesion area is an oval or an ellipsoid, a margin of the lesion area becomes a smooth pattern, and when an echo feature has a hyperechogenic feature, the breast lesion is more likely to be diagnosed as benign. Since a lesion area 910 included in the ultrasonic image 900 shown in FIG. 9 has the above-described feature of the benign lesion, the processor 420 may generate a diagnostic result such as "Benign" or "Possibly Benign" as the analysis result of the lesion area 610 of the ultrasonic image 600.

In the above-described example, the basis of diagnosing the lesion included in the ultrasonic image 900 as benign may be that the shape of the lesion area 910 is an oval or an ellipsoid and the margin of the lesion area has a smooth pattern. Accordingly, a shape 920 of the lesion area 910 and a margin area 930 having a smooth pattern in the lesion area 910 may be at least some areas in the ultrasonic image 900, which are the basis of the diagnostic result (specifically, the lesion is benign). Here, a line 920 indicating the shape 920 of the lesion area 910 may be displayed to overlap the contour 915 of the lesion area 910 or may be displayed in an area adjacent to the lesion area 910.

In the disclosed embodiment, the diagnostic image in which the areas (e.g., 920, and 930) that are the basis of diagnosing the lesion area 910 as benign are displayed is provided to the user, thereby allowing the user to trust the diagnostic result more and to diagnose the object more easily by referring to the diagnostic result and the first area.

Figure 10:
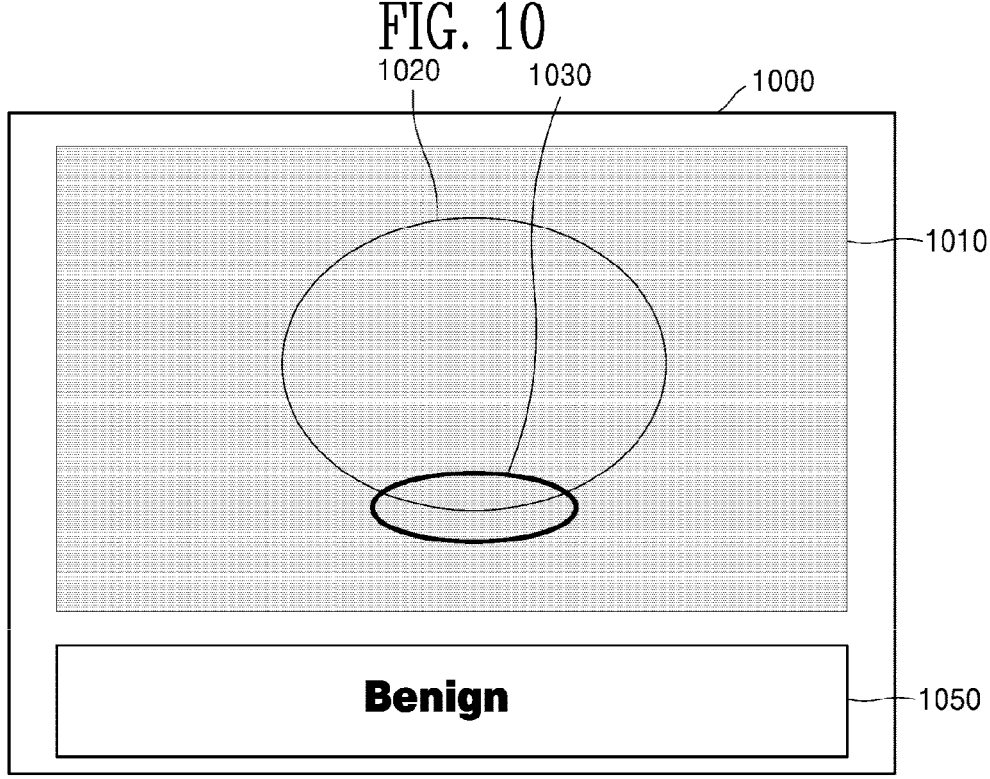
FIG. 10 is a diagram illustrating a user interface screen including another diagnostic image provided in an embodiment.

FIG. 10 is a diagram illustrating a user interface screen including another diagnostic image provided in an embodiment. Specifically, FIG. 7 illustrates a user interface screen 1000 output from the ultrasound diagnosis device 400. In addition, similar to FIGS. 8 and 9, FIG. 10 schematically illustrates a lesion area 1020 included in a diagnostic image 110. Here, a contour of the lesion area 1020 may correspond to the contour 915 of the lesion area of FIG. 9 identically.

Referring to FIG. 10, the user interface screen 1000 may include the diagnostic image 1010 and a diagnostic result 1050.

A portion that is the basis of determining a lesion imaged in the diagnostic image 1010 as "Benign" may be a portion having a smooth pattern of the margin of the lesion area 1020. Accordingly, the diagnostic image 1010 may be an image in which an area 730 having a smooth pattern is displayed as a first area in the margin of the lesion area 1020. The user may look at the diagnostic image 1010, which is an ultrasonic image including the lesion, to easily recognize a feature of the lesion (specifically, the margin having the smooth pattern) imaged in a first area (e.g., 1030). Thus, the user may quickly and easily determine whether the diagnostic result (e.g., "Benign") provided by the ultrasound diagnosis device is correct.

Figure 11:
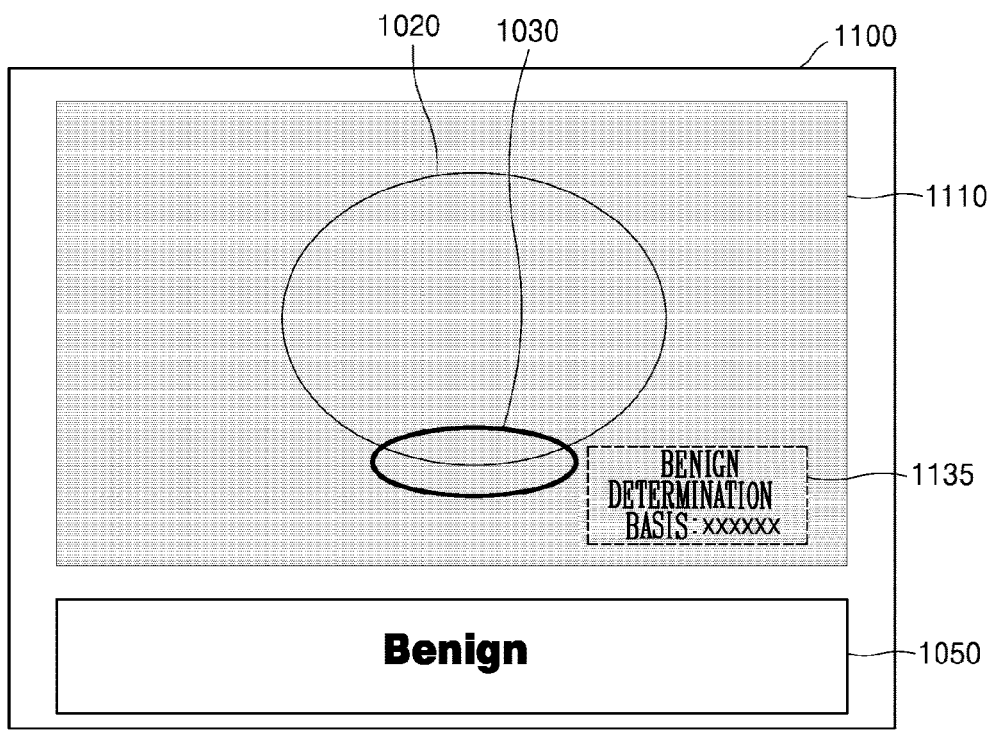
FIG. 11 is a diagram illustrating a user interface screen including another diagnostic image provided in an embodiment.

FIG. 11 is a diagram illustrating a user interface screen including another diagnostic image provided in an embodiment. Specifically, FIG. 11 illustrates a user interface screen 1100 output from the ultrasound diagnosis device 400. In the user interface screen 1100 shown in FIG. 11, the same components as in the user interface screen 1000 shown in FIG. 10 are illustrated using the same reference numerals.

In the disclosed embodiment, the processor 420 may display diagnostic information 1135, which is information on the feature of the lesion area (e.g., a margin feature of the lesion area) appearing in the first area (e.g., 1030), in the ultrasonic image, thereby generating a diagnostic image 1110.

For example, since the feature of the lesion area appearing in the first area 1030 becomes the margin feature of the lesion area, diagnostic information 1135 may be "Margin: smooth" which is information specifically indicating the margin feature. In addition, the diagnostic information may be "benign determination basis: Margin-smooth" which is information that is the basis of deriving malignant determination that is the diagnostic result.

Figure 12:
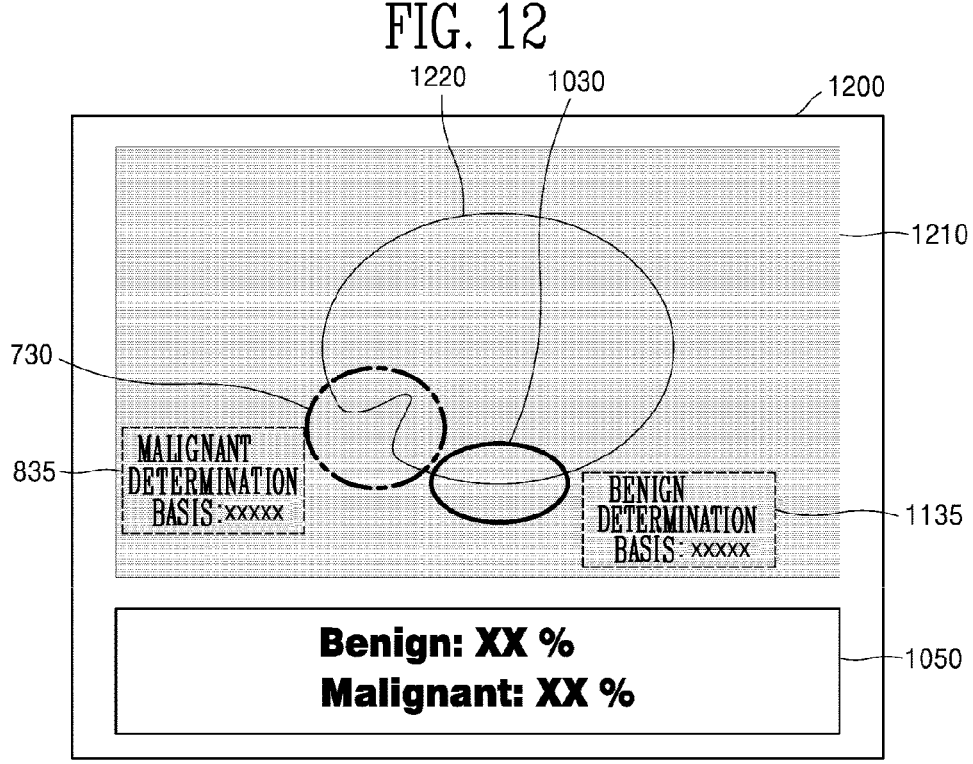
FIG. 12 is another diagram illustrating a user interface screen including another diagnostic image provided in an embodiment.

FIG. 12 is another diagram illustrating a user interface screen including another diagnostic image provided in an embodiment.

In the disclosed embodiment, as the analysis result of the lesion, the processor 420 may determine whether the diagnostic result has accuracy that is greater than or equal to a limit value, and when the diagnostic result having the accuracy that is greater than or equal to a limit value is not present, the processor 420 may derive at least two diagnostic results.

For example, when the diagnostic result, which is acquired as the analysis result of the lesion, has the accuracy of 90% or more, the processor 420 may output one diagnostic result. When the lesion 610 shown in FIG. 6 is determined as malignant with the accuracy of 90%, the processor 420 may determine the diagnostic result of the lesion 610 as "malignant."

In contrast, when the diagnostic result, which is acquired as the analysis result of the lesion, has the accuracy that is less than the limit value (e.g., 90%), the processor 420 may output a plurality of diagnostic results. For example, the diagnostic result 1050 with respect to the lesion 1220 may be displayed together with the diagnostic accuracy for each of the plurality of diagnostic results as in the user interface 1200. Also, when the plurality of diagnostic results are output, the processor 420 may output the plurality of diagnostic results in the order of high-to-low accuracy thereof.

An example in which, as the analysis result of the lesion area 1220 included in the ultrasonic image, a probability that the lesion 1220 is determined as being benign is 70% and a probability that the lesion 1220 is determined as being malignant is 30% will be described. In addition, an example in which the processor 420 sets the limit value corresponding to the accuracy of the diagnostic result to 90%. In this case, the diagnostic result 1050 with respect to the lesion 1220 may be displayed as "Benign: 30% and Malignant: 70%."

In addition, a diagnostic image 1210 may be an image in which both of the first area (e.g., 1030) that is the basis of the benign determination and the first area (e.g., 730) that is the basis of the malignant determination are displayed. In addition, similar to FIGS. 9 and 11, the diagnostic image 1210 may be an image in which the pieces of diagnostic information (e.g., 835 and 1135) corresponding to the first areas are additionally displayed.

Figure 13:
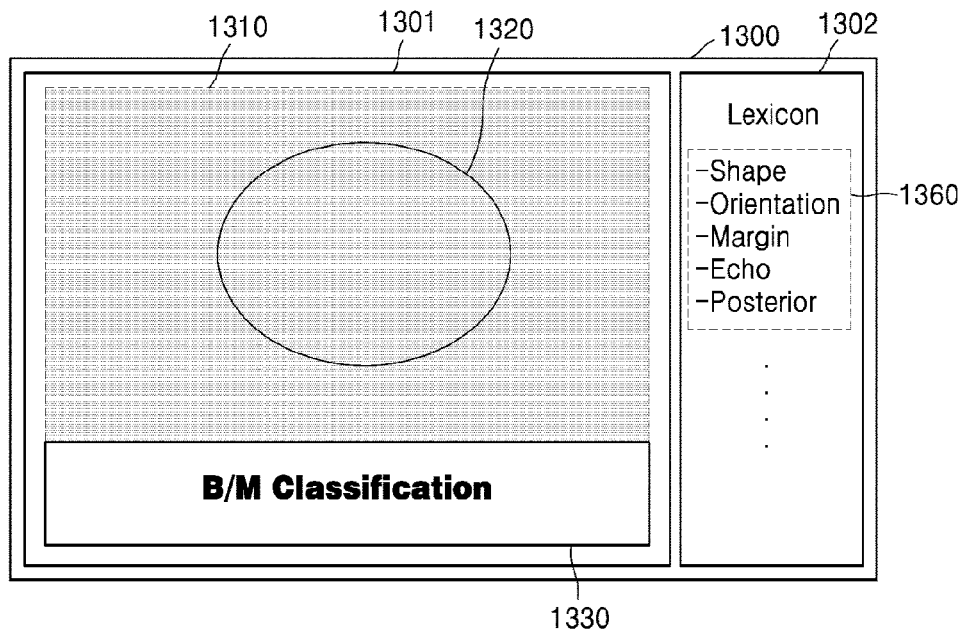
FIG. 13 is a diagram illustrating an example of the user interface screen provided in the embodiment.

FIG. 13 is a diagram illustrating an example of the user interface screen provided in the embodiment.

In the disclosed embodiment, the processor 420 may generate a user interface screen 1400 including a diagnostic image 1310, a diagnostic result 1330, and a list 1302 indicating features of a lesion area. In addition, the display 430 may display the user interface screen 1400 under the control of the processor 420.

In addition, the diagnostic image 1310 and the diagnostic result 1330 may be formed as one partial screen 1301. Specifically, the processor 420 may display the diagnostic result 1330 to overlap in a partial area of the diagnostic image 1310, thereby generating the diagnostic image 1310. In FIG. 13, the diagnostic result 1330 is classified into benign and malignant.

In addition, the list 1302 includes items corresponding to the features indicating the lesion. Here, each of the plurality of features is the feature of the lesion for distinguishing a type of a lesion and includes the above-described shape of the lesion area, the orientation of the lesion, the margin of the lesion, the echo feature appearing in the lesion area, and a posterior feature of the lesion area.

Specifically, the plurality of above-described features may correspond to a plurality of items included in a lexicon which is a standard term for ultrasound examination defined by the ACR. In this case, the list 1302 may include a plurality of items 1360 included in the lexicon.

In the drawings described and illustrated below, including FIG. 13, an example in which the list 1302 indicating the features of the lesion area is formed as a lexicon will be illustrated and described.

In an embodiment of the present disclosure, when a plurality of partial areas corresponding to the plurality of features are present, the processor 420 may generate a diagnostic image in which the plurality of partial areas are displayed to be distinguished from each other so as to distinguish the plurality of features from each other.

Alternatively, the processor 420 may generate the diagnostic image 1320 such that the first area corresponding to an item selected by the user from among the plurality of items 1360 included in the list 1302 is included in the diagnostic image 1320.

Specifically, in response to a user input for selecting any one among the plurality of items included in the list 1302, the processor 420 may display at least one partial area, which indicates a feature corresponding to the selected item, as the first area in the ultrasonic image, thereby generating the diagnostic image. Then, the processor 420 may update, generate, and display the user interface screen 1400 to reflect the generated diagnostic image.

When the ultrasound diagnosis device 400 displays the user interface screen 1300, the user may look at the user interface screen 1300 and may want to identify a partial area on the ultrasonic image in which any one among the plurality of features that are the basis of the diagnostic result 1330 appears. In this case, the user may select any one among the plurality of features that are the basis of the diagnostic result 1330 through the user interface 460. Specifically, the user may select an item corresponding to any one among the plurality of features included in the list 1302. Accordingly, the user interface 460 may receive a user input for selecting one item included in the list 1302. Then, on the basis of the user input received through the user interface 460, the processor 420 may identify a feature corresponding to the selected item and generate the diagnostic image to allow an area (specifically, the first area) indicating the identified feature to be displayed in the ultrasonic image.

That is, on the basis of the user input received through the user interface 460, the ultrasound diagnosis device 400 may output a user interface screen including a diagnostic image generated by displaying an area (specifically, the first area), which indicates a feature corresponding to the selected item in the ultrasonic image. Here, an area indicating a predetermined feature (specifically, the first area that is a partial area in the ultrasonic image) may mean an area that is the basis of determination or determining the predetermined feature. For example, when the shape feature of the lesion area is determined as an oval, the first area may be at least a partial contour area having a curvature corresponding to an ellipse among the lesion areas.

As described above, when the diagnostic image in which the first area indicating the feature selected on the basis of the user input is provided, the user may easily identify a partial area in the ultrasonic image in which the feature to be checked is displayed. Accordingly, convenience and ease for the user can be increased in diagnosing the lesion by the user.

In FIGS. 14 to 19 to be described below, components that are the same as in FIG. 13 are illustrated using the same reference numerals.

Figure 14:
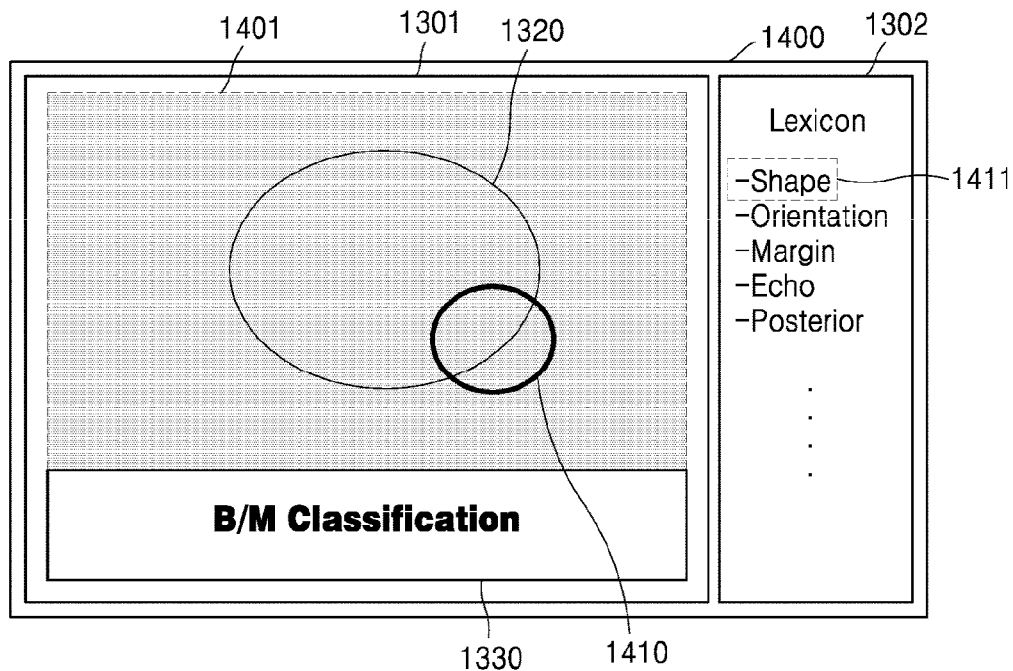
FIG. 14 is a diagram illustrating another example of the user interface screen provided in the embodiment.

FIG. 14 is a diagram illustrating another example of the user interface screen provided in the embodiment.

Referring to FIG. 14, a user interface screen 1400 may correspond to the user interface screen 1300.

A user input in which the user looks at the user interface screen 1300 and selects a "Shape" item included in the list 1302 may be input to the ultrasound diagnosis device 400. Then, the processor 420 may identify a partial area 1410 indicating a "shape" feature selected in response to the reception of the user input and control to output the user interface screen 1400 including a diagnostic image 1401 in which an identified partial area 1410 is displayed as a first area. In addition, although a case in which a partial area that is the basis of determining a predetermined feature is one has been illustrated as an example in FIG. 154, it is obvious that a plurality of partial areas that are the basis of determining the predetermined feature may exist.

In addition, in the user interface screen 1400, a selected item 1411 in the list 1302 may be displayed to be distinguished from unselected items (e.g., an orientation item, a margin item, an echo item, and a posterior item). For example, the processor 420 may generate the diagnostic image 1401 in which the selected item 1411 in the list 1302 is displayed to be distinguished from the unselected items (e.g., the orientation item, the margin item, the echo item, and the posterior item) using at least one among different colors, symbols, transparency, echo, marks, and lines of specific patterns.

Also, the processor 420 may generate a diagnostic image in which the diagnostic information (e.g., 835 or 1135) specifically indicating the feature of the selected item is displayed in an area corresponding to the partial area 1410. For example, when the shape feature of the lesion area appearing in the partial area 1410 is an "oval," the processor 420 may generate a diagnostic image (not shown) in which diagnostic information written as "Shape-Oval" is displayed in an area corresponding to the partial area 1410.

Figure 15:
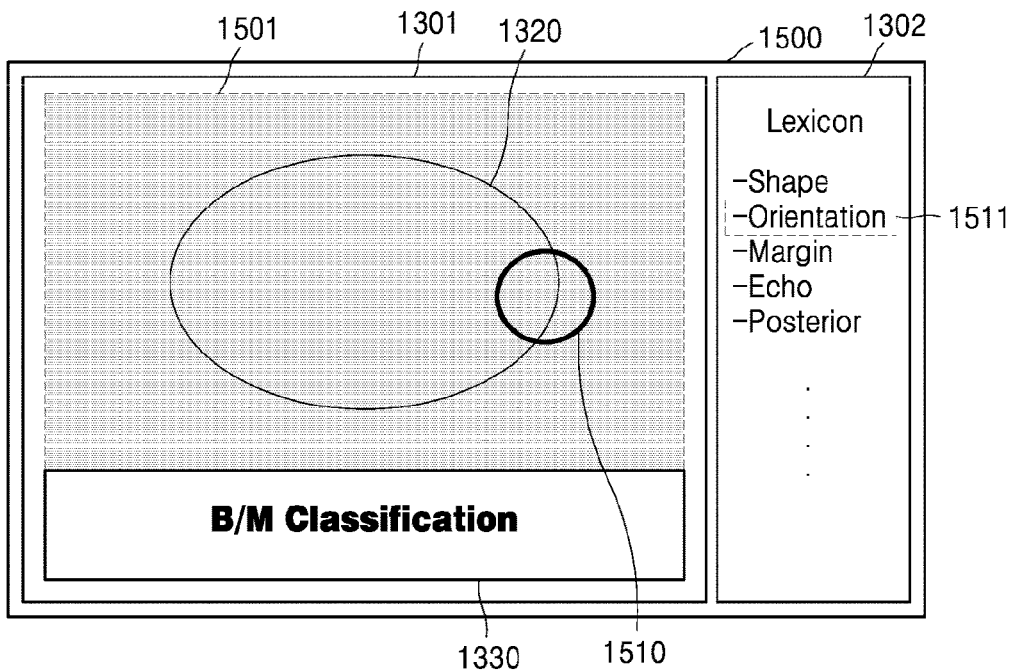
FIG. 15 is a diagram illustrating another example of the user interface screen provided in the embodiment.

FIG. 15 is a diagram illustrating another example of the user interface screen provided in the embodiment. Referring to FIG. 15, a user interface screen 1500 may correspond to the user interface screen 1300.

A user input in which the user looks at the user interface screen 1500 and selects an "Orientation" item 1511 included in the list 1302 may be input to the ultrasound diagnosis device 400. Then, the processor 420 may identify a partial area 1510 indicating an "orientation" feature selected in response to the reception of the user input and control to output the user interface screen 1500 including a diagnostic image 1501 in which an identified partial area 1510 is displayed as a first area.

Also, the processor 420 may generate a diagnostic image in which the diagnostic information (e.g., 835 or 1135) specifically indicating the feature of the selected item is displayed in an area corresponding to the partial area 1510. For example, when the orientation feature of the lesion area appearing in the partial area 1510 is "Parallel," the processor 420 may generate a diagnostic image (not shown) in which diagnostic information written as "Orientation-Parallel" is displayed in an area corresponding to the partial area 1510.

Figure 16:
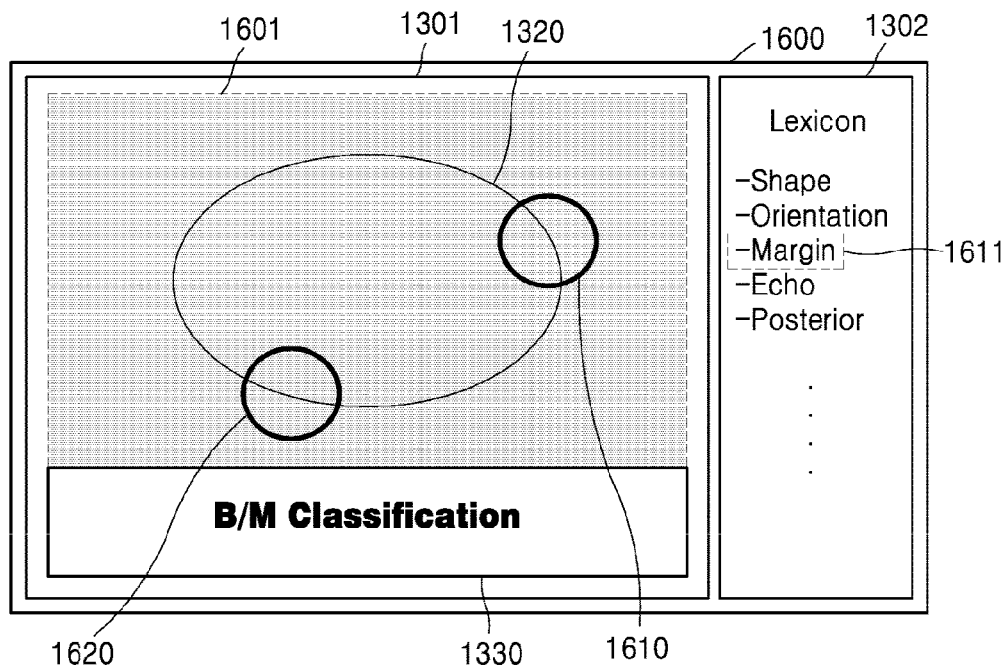
FIG. 16 is a diagram illustrating another example of the user interface screen provided in the embodiment.

FIG. 16 is a diagram illustrating another example of the user interface screen provided in the embodiment. Referring to FIG. 16, a user interface screen 1600 may correspond to the user interface screen 1300.

A user input in which the user looks at the user interface screen 1600 and selects a "Margin" item 1611 included in the list 1302 may be input to the ultrasound diagnosis device 400. Then, the processor 420 may identify partial areas 1610 and 1620 indicating a "Margin" feature selected in response to the reception of the user input and control to output the user interface screen 1600 including a diagnostic image 1601 in which the identified partial area 1610 and 1620 are displayed as a first area.

In addition, the processor 420 may generate a diagnostic image in which the diagnostic information (e.g., 835 or 1135) specifically indicating the feature of the selected item is displayed in areas corresponding to the partial areas 1610 and 1620. For example, when the margin feature of the lesion area appearing in the partial areas 1610 and 1620 is "smooth," the processor 420 may generate a diagnostic image (not shown) in which diagnostic information written as "Margin-smooth" is displayed in the areas corresponding to the partial areas 1610 and 1620.

Figure 17:
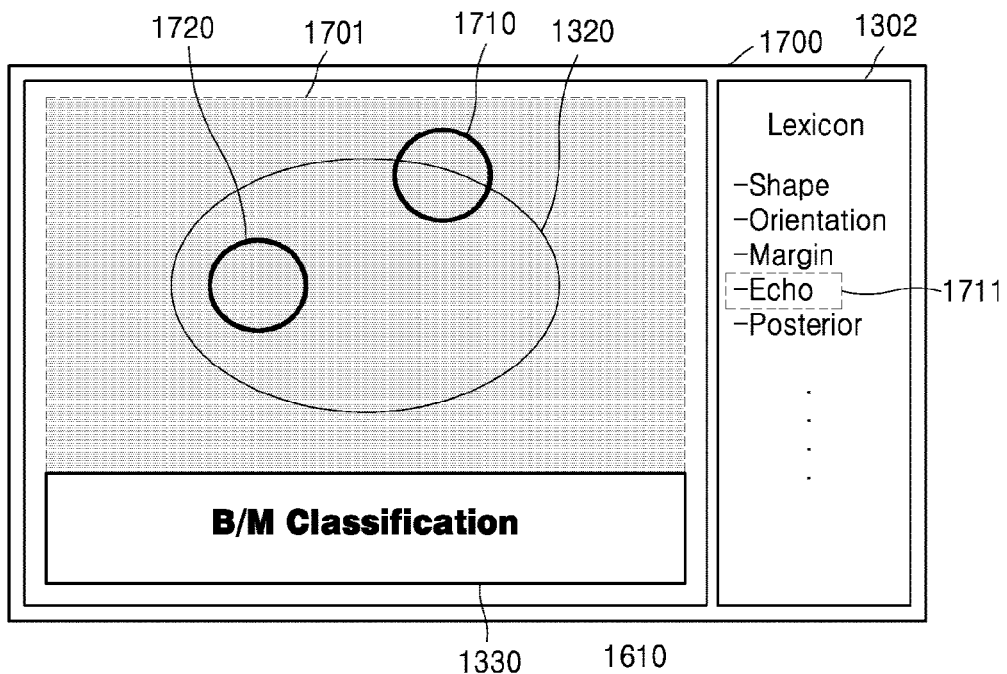
FIG. 17 is a diagram illustrating another example of the user interface screen provided in the embodiment.

FIG. 17 is a diagram illustrating another example of the user interface screen provided in the embodiment. Referring to FIG. 17, a user interface screen 1700 may correspond to the user interface screen 1300.

A user input in which the user looks at the user interface screen 1700 and selects an "Echo" item 1711 included in the list 1302 may be input to the ultrasound diagnosis device 400. Then, the processor 420 may identify partial areas 1710 and 1720 indicating an "echo" feature selected in response to the reception of the user input and control to output the user interface screen 1700 including a diagnostic image 1701 in which the identified partial area 1710 and 1720 are displayed as a first area.

In addition, the processor 420 may generate a diagnostic image in which the diagnostic information (e.g., 835 or 1135) specifically indicating the feature of the selected item is displayed in areas corresponding to the partial areas 1710 and 1720. For example, when the echo feature of the lesion area appearing in the partial areas 1710 and 1720 is "hyperechoic," the processor 420 may generate a diagnostic image (not shown) in which diagnostic information written as "Echo-hyperechoic" is displayed in the areas corresponding to the partial areas 1710 and 1720.

Figure 18:
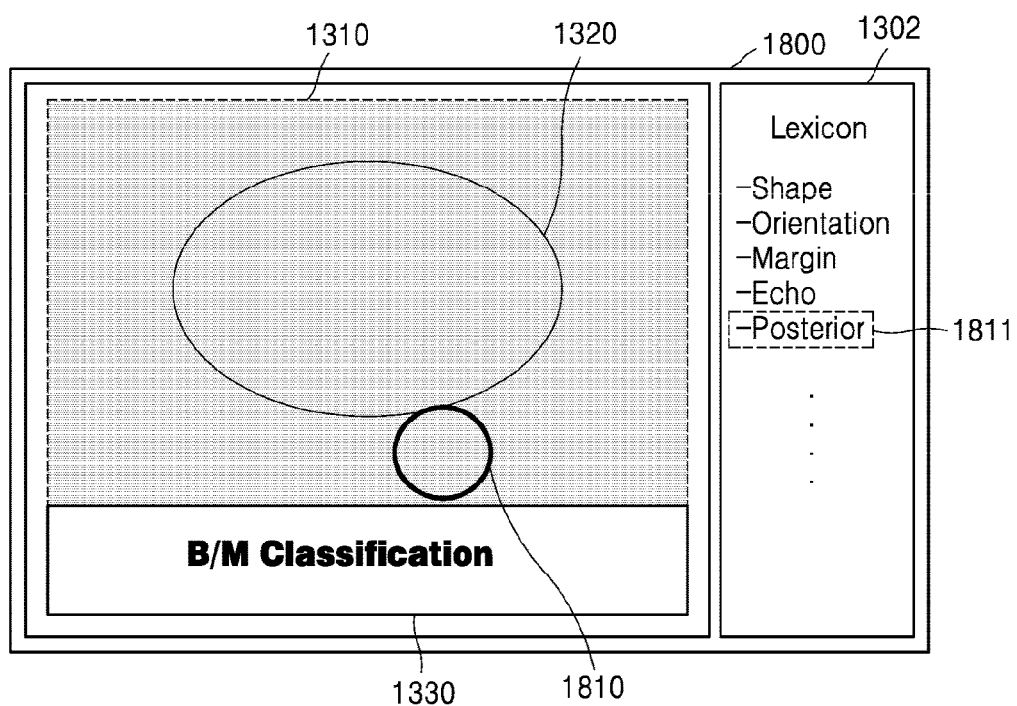
FIG. 18 is a diagram illustrating another example of the user interface screen provided in the embodiment.

FIG. 18 is a diagram illustrating another example of the user interface screen provided in the embodiment. Referring to FIG. 18, a user interface screen 1800 may correspond to the user interface screen 1300.

A user input in which the user looks at the user interface screen 1800 and selects a "Posterior" item 1811 included in the list 1302 may be input to the ultrasound diagnosis device 400. Then, the processor 420 may identify a partial area 1810 indicating a "posterior" feature selected in response to the reception of the user input and control to output the user interface screen 1800 including a diagnostic image 1801 in which an identified partial area 1810 is displayed as a first area.

For example, when the object is the abdomen including the gallbladder, a lesion area is identified, and an outer area of the identified lesion area (specifically, a posterior area of the lesion area) is imaged very darkly within the ultrasonic image, it may be determined that a stone is present as a lesion in the gallbladder. In the above example, when a "posterior" feature is selected, the processor 420 may generate a diagnostic image in which a very darkly imaged area of the outside area of the identified lesion area is displayed as a first area.

Also, the processor 420 may generate a diagnostic image in which the diagnostic information (e.g., 835 or 1135) specifically indicating the feature of the selected item is displayed in an area corresponding to the partial area 1810. For example, when the posterior feature of the lesion area appearing in the partial area 1810 is "No Posterior Findings," the processor 420 may generate a diagnostic image (not shown) in which diagnostic information written as "No Posterior Findings" is displayed in an area corresponding to the partial area 1810.

Figure 19:
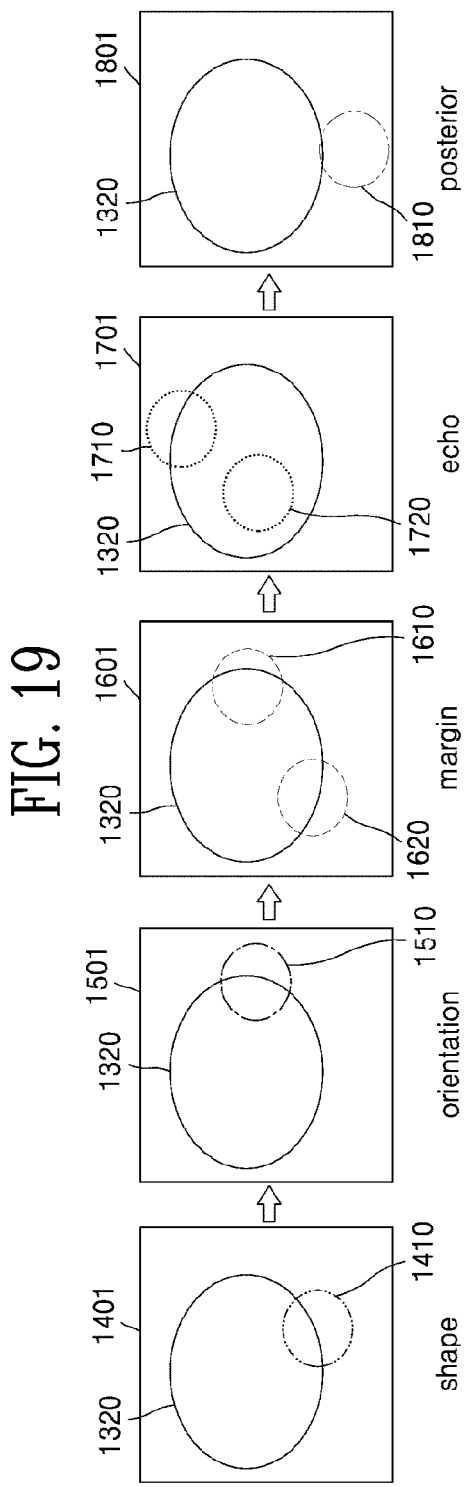
FIG. 19 is a diagram illustrating another example of the user interface screens provided in the embodiment.

FIG. 19 is a diagram illustrating another example of the user interface screens provided in the embodiment. In FIG. 19, components that are the same as in FIGS. 13 to 18 are illustrated using the same reference numerals.

In the disclosed embodiment, the processor 420 may generate and display a user interface screen such that a plurality of diagnostic images corresponding to a plurality of features, each indicating a lesion result, are sequentially displayed.

Specifically, the processor 420 may generate and display the diagnostic image such that features corresponding to items included in the list 1302 are sequentially displayed. For example, the processor 420 may control the ultrasound diagnosis device 400 to sequentially display the diagnostic image 1401 shown in FIG. 14, the diagnostic image 1501 shown in FIG. 15, the diagnostic image 1601 shown in FIG. 16, the diagnostic image 1701 shown in FIG. 17, and the diagnostic image 1801 shown in FIG. 18.

In addition, the display order among the diagnostic image 1401, the diagnostic image 1501, the diagnostic image 1601, the diagnostic image 1701, and the diagnostic image 1801 may be determined on the basis of a user setting, a proprietary setting of the processor 420, importance between the plurality of features, or influences of the plurality of features on the diagnostic result.

Figure 20:
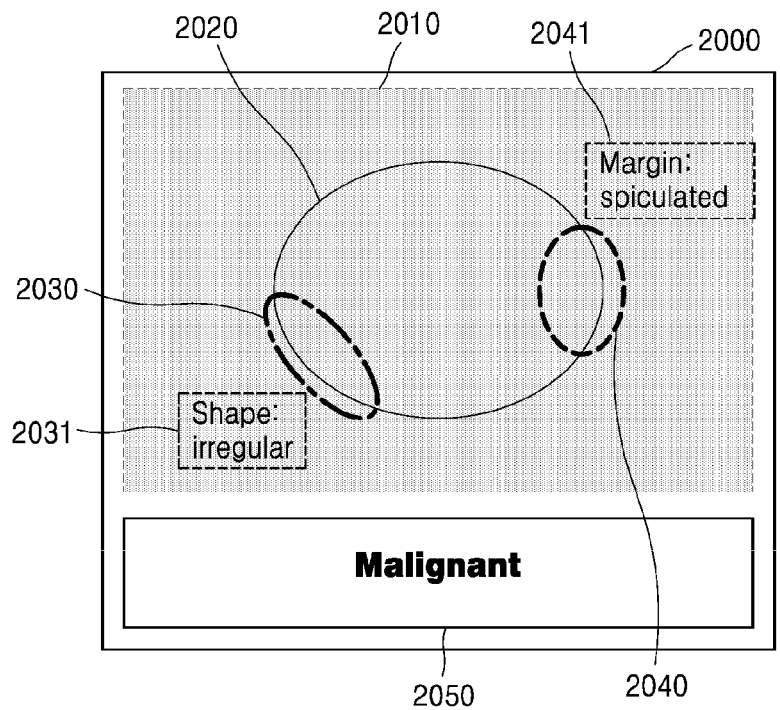
FIG. 20 is a diagram illustrating another example of the user interface screen provided in the embodiment.

FIG. 20 is a diagram illustrating another example of the user interface screen provided in the embodiment. Referring to FIG. 20, a user interface screen 2000 may correspond to the user interface screen 1300 shown in FIG. 13. As described with reference to FIG. 13, the user may select at least two items from among the plurality of items corresponding to the plurality of features included in the list 1302. Accordingly, the processor 420 may control to generate and display a user interface screen 2000 including a diagnostic image 2010, in which partial areas indicating the plurality of features are displayed, and a diagnostic result 2050.

For example, when the margin item and the shape item included in the list 1302 are selected through a user input, the processor 420 may control to generate and display the diagnostic image 2010 in which a partial area 2040 that is the basis of determining a margin feature is displayed to be distinguished from a partial area 2030 that is the basis of determining a shape feature. In addition, the processor 420 may generate the diagnostic image 2010 in which diagnostic information (e.g., 2041) is displayed to overlap an area corresponding to the partial area (e.g., 2040). In addition, in FIG. 20, a case in which the partial area 2040 and the partial area 2030 are distinguished through patterns of different dotted lines is illustrated as an example.

In addition, when the user does not select a specific item (or a feature), the processor 420 may generate the diagnostic image (e.g., 2010) in which partial areas indicating two or more of the features among the plurality of features are displayed on the basis of a user setting, a proprietary setting of the processor 420, importance among a plurality of features, or influences of the plurality of features on the diagnostic result. Specifically, the processor 420 may display the partial areas in the diagnostic image using at least one among a specific color, a symbol, transparency, an echo, a mark, and a line having a specific pattern to distinguish the plurality of features from each other.

For example, the processor 420 displays a partial area indicating the shape feature of a lesion area with a red dotted line, displays a partial area indicating an orientation feature of a lesion with a blue dotted line, displays a partial area indicating a margin feature of the lesion with a green dotted line, displays a partial area indicating an echo feature appearing in the lesion area with a yellow dotted line, and displays a partial area indicating a posterior feature of the lesion area with a purple dotted line so that it is possible to generate a diagnostic image in which different features are distinguished from each other.

Figure 21:
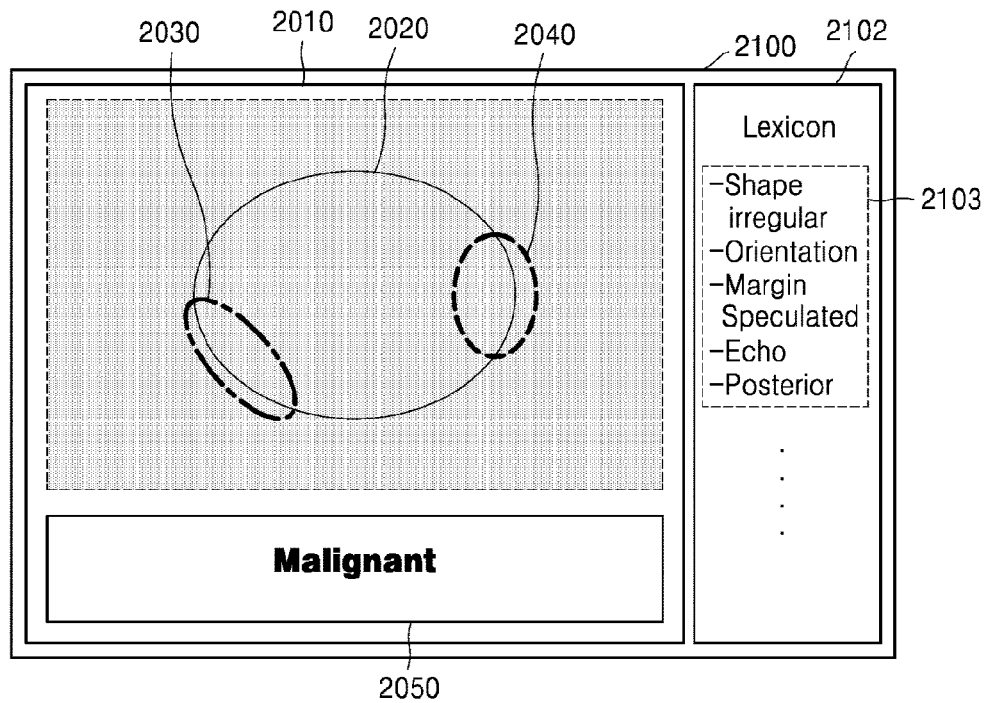
FIG. 21 is a diagram illustrating another example of the user interface screen provided in the embodiment.

FIG. 21 is a diagram illustrating another example of the user interface screen provided in the embodiment. In FIG. 21, components that are the same as in FIG. 20 are illustrated using the same reference numerals.

In the disclosed embodiment, in a list 2102, a plurality of items may include information specifically representing features corresponding to the plurality of items. For example, a shape item may include information of "irregular," which is a feature specifically describing the shape feature, and a margin item may include information of "spiculated."

In addition, the processor 420 may control each of the plurality of items included in the list 2102 to be displayed to match at least one partial area corresponding thereto. Specifically, the processor 420 may display each of the plurality of items to match at least one partial area corresponding thereto using at least one among different colors, marks, symbols, transparency, echo, types of dotted lines, and thicknesses of the dotted lines.

For example, a case in which the partial image 2030 is a partial image that is the basis of determining the shape feature, and the partial image 2040 is a partial image that is the basis of determining the margin feature will be described as an example. In this case, the processor 420 may control the partial image 2030 and the shape item in the list 2102 to be displayed with at least one among the same color, the same mark, the same symbol, the same transparency, the same echo, the same type of dotted line, and the same thickness of the dotted line. In addition, the processor 420 may control the partial image 2040 and the margin item in the list 2102 to be displayed with at least one among the same color, the same mark, the same symbol, the same transparency, the same echo, the same type of dotted line, and the same thickness of the dotted line. In this case, the shape item and the margin item may be displayed with at least one among colors, marks, symbols, transparency, echoes, types of dotted lines, and thicknesses of the dotted lines, which are distinguished from each other.

In addition, the diagnostic result 2050 may be determined and displayed as malignant on the basis of the fact that the shape of the lesion area is irregular and the margin thereof is spiculated.

Figure 22:
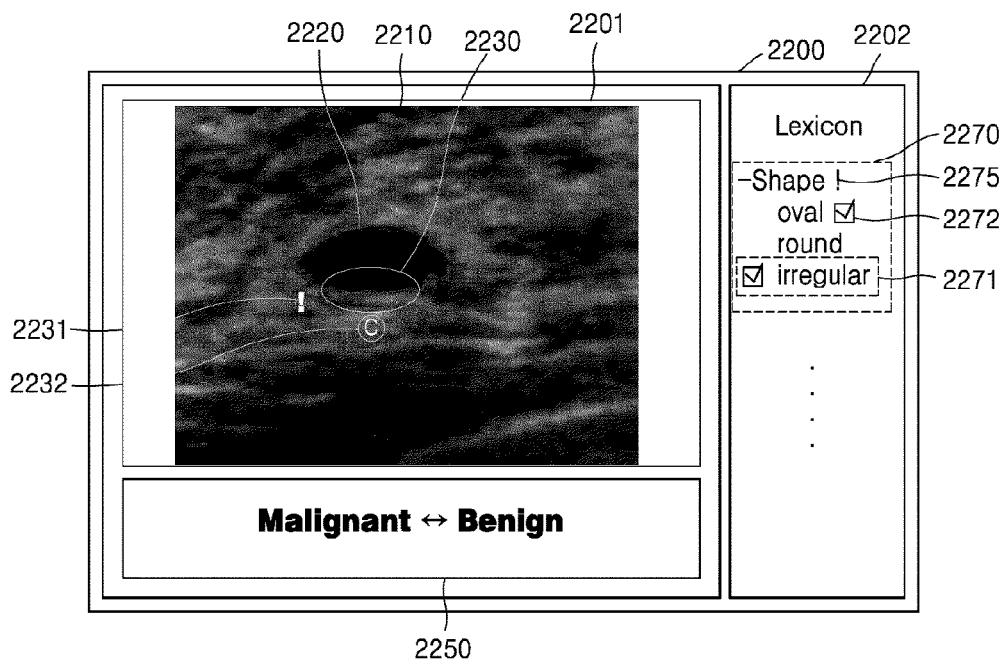
FIG. 22 is a diagram illustrating another example of the user interface screen provided in the embodiment.

FIG. 22 is a diagram illustrating another example of the user interface screen provided in the embodiment.

Referring to FIG. 22, the processor 420 may generate a user interface screen 1400 including a diagnostic image 2210, a diagnostic result 2250, and a list 2202 indicating features of a lesion area.

In the disclosed embodiment, when a predetermined feature included in the list 2202 is changed and thus a diagnostic result is changed, the processor 420 may distinguish the predetermined feature included in the list 2203 from other features.

When the feature of the partial area included in the lesion area is changed, there may exist a case in which the diagnostic result is changed. That is, there may exist a case in which a feature capable of changing the diagnostic result by affecting the determination of the diagnostic result (e.g., benign or malignant) exists. Hereinafter, the feature capable of changing the diagnostic result is referred to as a "major feature." In addition, a partial area indicating the major feature in the ultrasonic image is separately referred to as a second area.

For example, the processor 420 may acquire a contour area of a lesion and a contour of the lesion and acquire at least one feature among a shape of the lesion, an orientation of the lesion, a shape of the margin of the lesion, an echo with respect to a lesion area, and a posterior feature of the lesion area on the basis of the acquired the contour of the lesion.

Here, there may exist a case in which a section in which the contour of the lesion is unclear exists. For example, there may exist a case in which the contour of the lesion is unclear in a partial area (e.g., 2230) within a lesion area 2220. In this case, in the partial area 2230, the processor 420 may acquire a first contour as the contour of the lesion or acquire a second contour as the contour of the lesion. In this case, the shape of the lesion may be determined as being oval on the basis of the first contour, and the shape of the lesion may be determined as being irregular on the basis of the second contour. That is, when the contour of the lesion in the partial area (e.g., 2230) is changed, and when a feature that is the basis of the diagnostic result is changed, the processor 420 may control a diagnostic image 2201, in which the partial area (e.g., 2230) is displayed, to be displayed.

In addition, the processor 420 may generate a diagnostic image by displaying a portion in which the contour of the lesion is unclear in the ultrasonic image. Here, the "portion in which the contour of the lesion is unclear" may be a portion in which accuracy of the extracted contour has a value that is less than or equal to a limit value. Specifically, the processor 420 may display the contour extracted from the portion in which the contour of the lesion is an unclear area (e.g., 2230) to be distinguished from a contour of a portion which is not unclear (e.g., a portion other than 2230), thereby generating and displaying the diagnostic image 2201.

Referring to FIG. 22, the processor 420 may extract the lesion area 2220 having the illustrated contour. Here, a portion in which the extracted contour is unclear may be displayed as the partial area 2230. Then, as shown in FIG. 22, the processor 420 may control the diagnostic image 2201, in which the partial area 2230 is displayed, to be displayed.

Specifically, as the analysis result of the lesion area 2220 having the illustrated contour, the processor 420 may determine a shape feature appearing in the partial area 2230 as being irregular. However, when the shape feature appearing in the partial area 2230 is changed to oval, there may exist a case in which the diagnostic result 2250 is changed from malignant to benign. Specifically, when the contour in the partial area 2230 is changed, the shape feature may be changed to oval, and when the shape feature is changed to the oval, the diagnostic result 2250 may be changed from malignant to benign. In this case, the shape feature may be the above-described major feature.

In the disclosed embodiment, the processor 420 may add an indication (e.g., a mark 2275) for distinguishing the major feature appearing in the above-described unclear area (e.g., 2230) from other features in the list 2202, thereby controlling the list 2202 to be generated and displayed. In addition, in an item corresponding to the major feature in the list 2202, the processor 420 may add an indication (e.g., a mark 2272) for distinguishing a currently acquired shape feature 2271 from other features (e.g., oval).

In addition, in the disclosed embodiment, when the contour of the lesion area extracted by the processor 420 includes the unclear portion (e.g., a section in which the accuracy of the contour is less than or equal to a limit value) (e.g., 2230), the processor 420 may control to display an icon 2232 for performing manual correction or contour re-extraction of an area corresponding to the partial area 2230. For example, the icon 2232 may be expressed as a "c" mark indicating correction. Here, the manual correction may mean an operation in which a user manually corrects an unclear contour portion. Specifically, when a user input for selecting the icon 2232 is received, the processor 420 may control to output a user interface screen including an edit window (not shown) for correcting a contour within the partial area 2230. As another example, when the icon 2232 is an icon for re-extraction of the contour, and when a user input for selecting the icon 2232 is received, the processor 420 may perform an automatic diagnostic operation, such as a CAD operation, to re-extract the contour and generate and display a diagnostic image including a lesion area formed by the re-extracted contour. In addition, the icon 2232 may be displayed in the partial area 2230, which is an area requiring contour correction, or displayed at a position adjacent to the partial area 2230.

In addition, in the disclosed embodiment, when a feature (i.e., a major feature) appearing in at least a partial area (e.g., 2230) included in the lesion area is changed and thus the diagnostic result is changed, the processor 420 may display the at least a partial area (e.g., 2230) in an ultrasonic image, thereby generating the diagnostic image 2230. Hereinafter, for convenience of description, the above-described "at least a partial area (e.g., 2230)" will be referred to as a "second area." In addition, the processor 420 may allow the user interface screen 2200 to include at least one among a symbol, a mark, and information which indicate that the diagnostic result may be changed. Specifically, the processor 420 may control the at least one among a symbol, a mark, and information, which indicate that the diagnostic result is changed when a feature appearing in the second area 2230 is changed, to be displayed in at least one among the diagnostic image 2201, the diagnostic result 2250, and the list 2202.

Referring to FIG. 22 as an example, the processor 420 may detect the partial area 2230 that is the basis of determining a shape feature of the lesion area 2220. As the analysis result of the lesion area 2220, the processor 420 may determine the shape feature appearing in the partial area 2230 as being irregular. However, when the shape feature appearing in the partial area 2230 is changed to oval, there may exist a case in which the diagnostic result 2250 is changed from malignant to benign. That is, the shape feature may be the major feature.

In this case, the processor 420 may display an indication (e.g., the mark 2275) in the list 2202 for distinguishing the major feature from other features in the list 2202. In addition, in an item corresponding to the major feature in the list 2202, the processor 420 may add the indication (e.g., the mark 2272) for distinguishing a currently determined shape feature 2271 from other features (e.g., oval).

In addition, in displaying the diagnostic result 2250, information indicating that the diagnostic result may be changed may be displayed.

In addition, when a plurality of major features are present among a plurality of features that are the basis of diagnosing a lesion, the processor 420 may display a plurality of second areas in the diagnostic image so as to distinguish the plurality of major features from each other. For example, when major features are a shape feature and a margin feature, the processor 420 may generate and display a diagnostic image in which a second area corresponding to the shape feature is displayed to be distinguished from a second area corresponding to the margin feature.

In addition, in determining whether the major feature exists, the processor 420 may consider whether a specific determination of a predetermined feature has accuracy that is greater than or equal to a limit value. Specifically, in the shape feature, an example in which, when the shape feature is determined as being oval, the accuracy is 70% and the limit value is 90% will be described. When the accuracy of determining that the shape feature is oval is 90%, since the accuracy has a value that is greater than and equal to the limit value, the processor 420 may not determine the shape feature as the major feature.

However, when the accuracy of determining that the shape feature is oval is 70%, since the accuracy has a value that is less than the limit value, the processor 420 may determine the shape feature as the major feature. Accordingly, when a predetermined feature determined as the major feature exists, the processor 420 may control the user interface screen 2200 to include at least one among the second area (e.g., 2230) indicating the major feature, an item (e.g., 2270) including detailed information on the major feature, and an indication indicating the presence of the major feature (e.g., the mark (2231 or 2275)).

Figure 23:
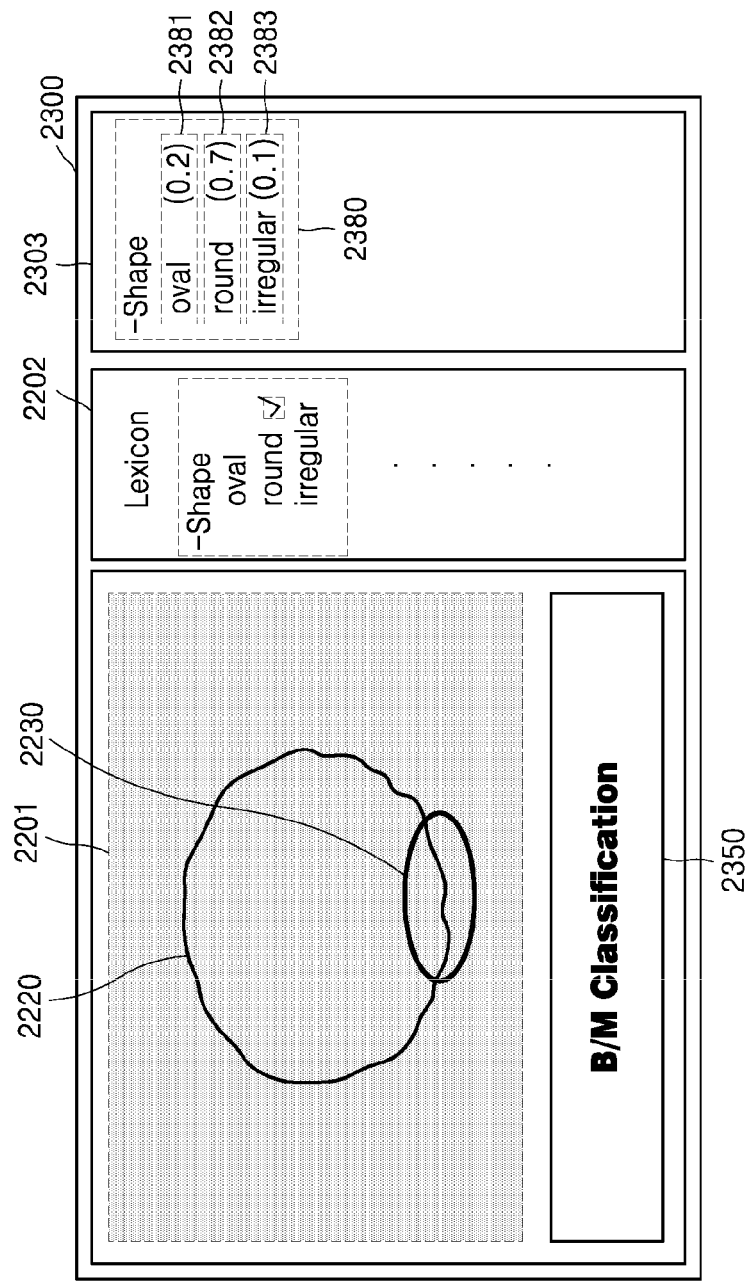
FIG. 23 is a diagram illustrating another example of the user interface screen provided in the embodiment.

FIG. 23 is a diagram illustrating another example of the user interface screen provided in the embodiment.

Figure 24:
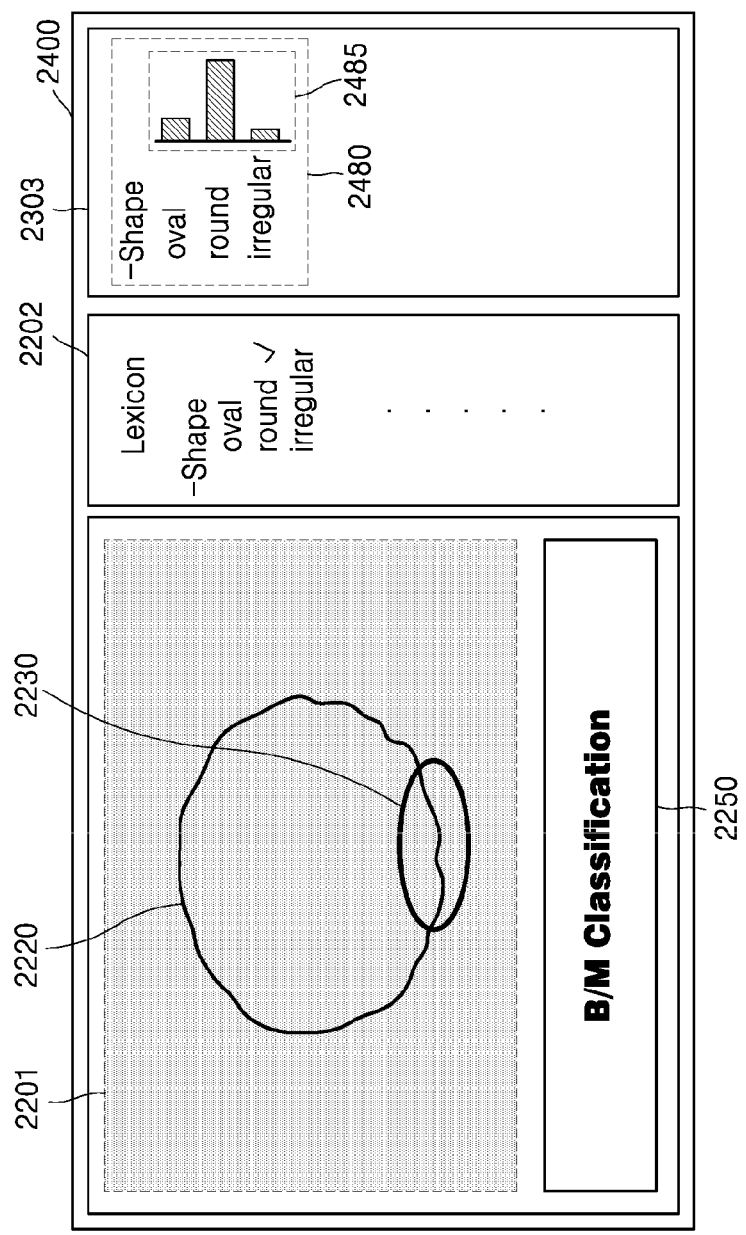
FIG. 24 is a diagram illustrating another example of the user interface screen provided in the embodiment.

FIG. 24 is a diagram illustrating another example of the user interface screen provided in the embodiment.

In FIGS. 23 and 24, the lesion area (e.g., 2220) included in the diagnostic image (e.g., 2201) is simplified and schematically illustrated. In addition, in FIGS. 23 and 24, components that are the same as in FIG. 22 are illustrated using the same reference numerals.

Referring to FIG. 23, when compared with the user interface screen 2200, a user interface screen 2300 may further include a sub screen 2302 including detailed information 2380 corresponding to the major feature.

Here, the detailed information 2380 may include information indicating determination accuracy on the major feature (or a diagnosis probability). Specifically, an example in which a diagnosis probability of a shape feature to be determined as being oval is 20% (or 0.2), a diagnosis probability of a shape feature to be determined as being round is 70% (or 0.2), and a diagnosis probability of a shape feature to be determined as being irregular is 10% (or 0.2) will be described. Then, the processor 420 may control the information 2380 indicating the determination accuracy on the major feature to be generated and displayed on the user interface screen 2300. Specifically, the information 2380 may include the diagnosis probability to be determined as being oval 2381, the diagnosis probability to be determined as being round 2382, and the diagnosis probability to be determined as being irregular 2383. In addition, the diagnosis probability to be determined as being oval 2381, the diagnosis probability to be determined as being round 2382, and the diagnosis probability to be determined as being irregular 2383 may be displayed in the order of increasing probability values.

Referring to FIG. 24, information 2480 included in a user interface screen 2400 may correspond to the information 2380 shown in FIG. 23. Here, the information 2480 includes the same content as the information 2380 and, alternatively, may be expressed in a different format. For example, the diagnosis probability to be determined as being oval 2381, the diagnosis probability to be determined as being round 2382, and the diagnosis probability to be determined as being irregular 2383 may be expressed as a graph form 2485 in the user interface 2400 shown in FIG. 24.

In the disclosed embodiment, when the ultrasound diagnosis device 400 outputs an ultrasonic image including a lesion area, in response to a user input in which one position or a predetermined partial area of the lesion area is selected, the processor 420 may control to generate or display a diagnostic image in which information on a feature of a lesion appearing in the selected position or the partial area or information that is the basis of a diagnostic result is displayed to overlap the ultrasonic image.

Figure 25:
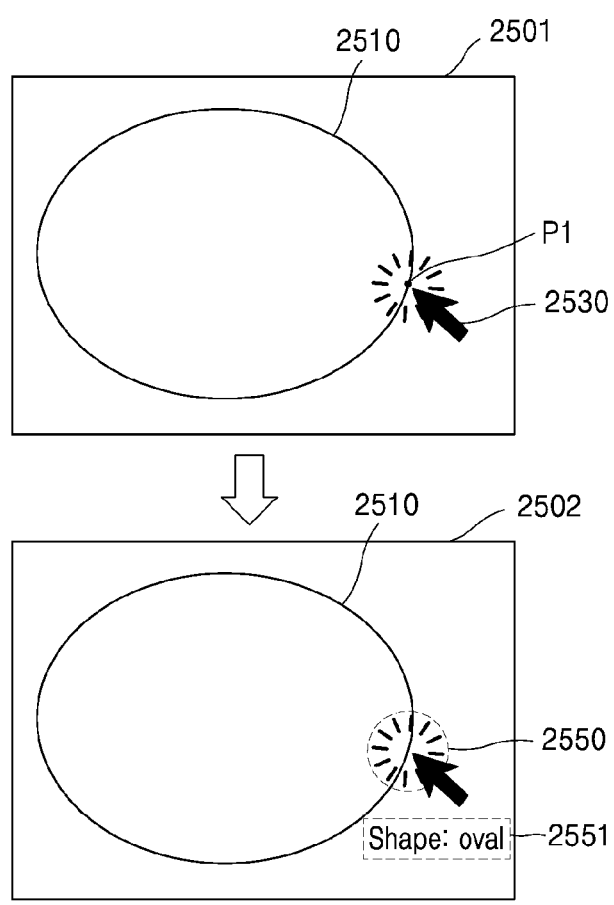
FIG. 25 is a diagram illustrating a diagnostic image output in response to a user input.

FIG. 25 is a diagram illustrating a diagnostic image output in response to a user input.

Figure 26:
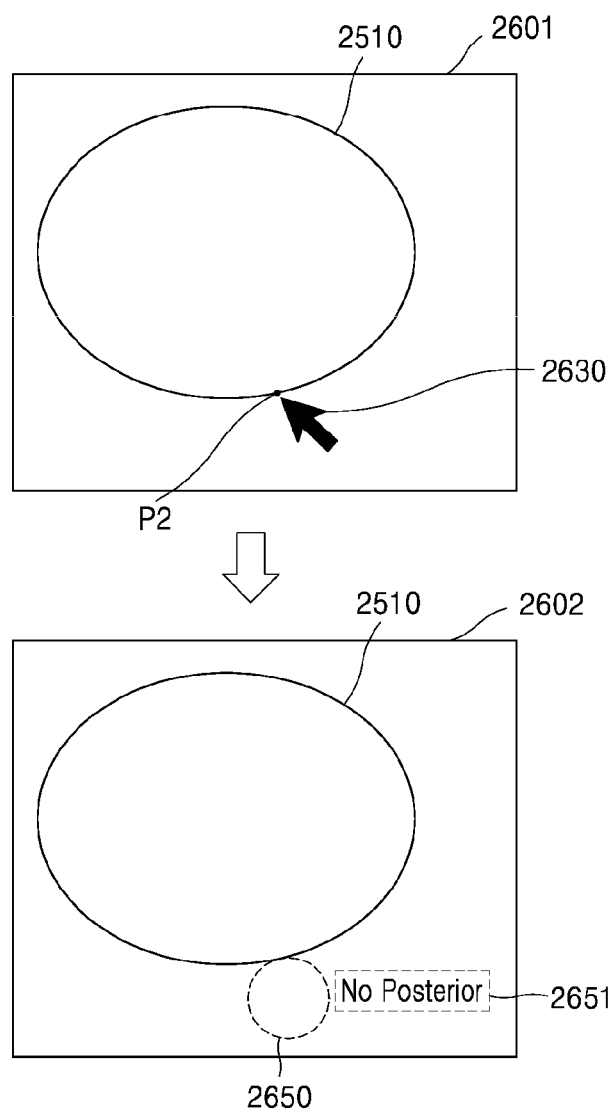
FIG. 26 is another diagram illustrating the diagnostic image output in response to the user input.

FIG. 26 is another diagram illustrating the diagnostic image output in response to the user input.

Figure 27:
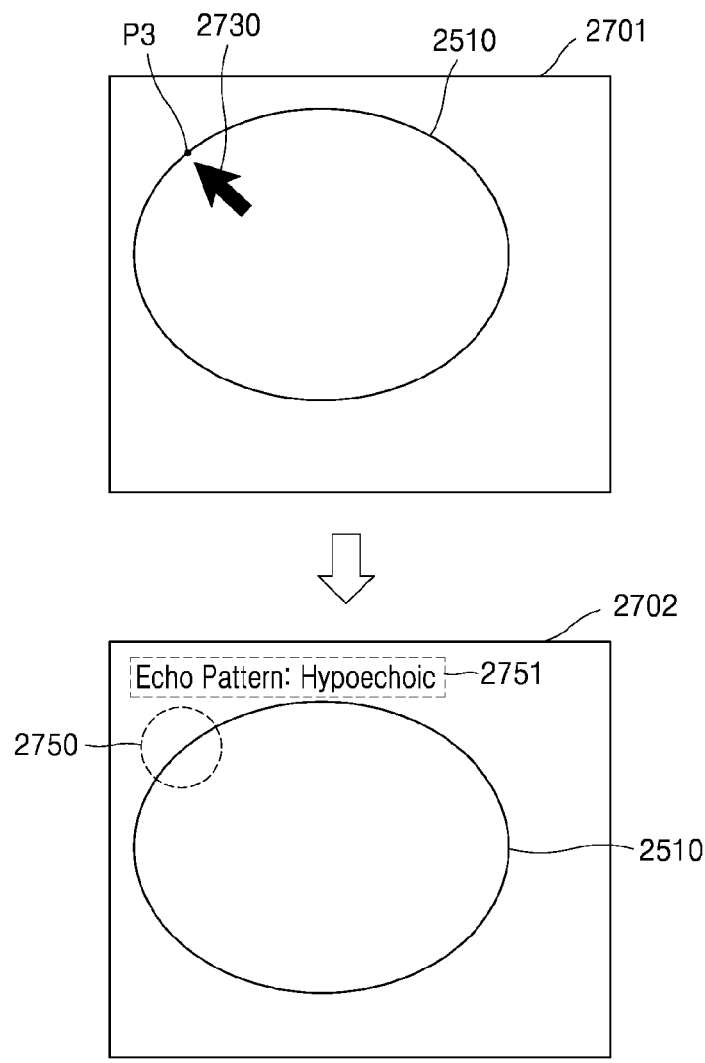
FIG. 27 is another diagram illustrating the diagnostic image output in response to the user input.

FIG. 27 is another diagram illustrating the diagnostic image output in response to the user input.

In FIGS. 25 to 27, the same components are illustrated using the same reference numerals. In addition, an arrow marker (e.g., 2530) shown in FIGS. 25 to 27 indicates a position or a partial region, which is selected or pointed at through a user input. In addition, in FIGS. 25 to 27, an ultrasonic image (e.g., 2501) includes a lesion area 2510. In addition, in FIGS. 25 to 27, the ultrasonic image 2501, an ultrasonic image 2601, and an ultrasonic image 2701 may correspond to each other identically.

Referring to FIG. 25, the ultrasound diagnosis device 400 may display the ultrasonic image 2501 including the lesion area 2510. In addition, the user may select a position or an area, at which the user specifically want to look, in the ultrasonic image 2501. Here, a selection operation may be performed by manipulating (e.g., clicking or double clicking) a selection part such as a cursor or a pointer, which is included in the user interface 460, to select a predetermined position or area. In addition, when a cursor or a pointer for selection is located on the ultrasonic image 2501, the processor 420 may recognize that a corresponding position is selected. In FIGS. 25 to 27, a location of the selection part for selection is illustrated as an arrow (e.g., 2530, 2630, or 2730).

Referring to FIG. 25, when a predetermined position P1 on the lesion area 2510 included in the ultrasonic image 2501 is selected, the processor 420 may control to generate and display a diagnostic image 2502 in which at least one of a partial area 2550 corresponding to the position P1 selected in response to a selection input and information 2551 on a feature appearing in the partial area is displayed. For example, when the partial area 2550 corresponding to the selected position P1 is an area indicating a shape feature among a plurality of features deriving a diagnostic result, the information 2551 such as "Shape: Oval" may be displayed in the diagnostic image 2502.

Referring to FIG. 26, when a predetermined position P2 on the lesion area 2510 included in the ultrasonic image 2601 is selected, the processor 420 may control to generate and display a diagnostic image 2602 in which at least one of a partial area 2650 corresponding to the position P2 selected in response to a selection input and information 2651 on a feature appearing in the partial area is displayed. For example, when the partial area 2550 corresponding to the selected position P2 is an area indicating a posterior feature among a plurality of features deriving a diagnostic result, the information 2651 such as "No Posterior" may be displayed in the diagnostic image 2602.

Referring to FIG. 27, when a predetermined position P3 on the lesion area 2510 included in the ultrasonic image 2701 is selected, the processor 420 may control to generate and display a diagnostic image 2702 in which at least one of a partial area 2750 corresponding to the position P3 selected in response to a selection input and information 2751 on a feature appearing in the partial area is displayed. For example, when the partial area 2750 corresponding to the selected position P3 is an area indicating an echo feature among a plurality of features deriving a diagnostic result, the information 2751 such as "Echo Pattern: Hypoechoic" may be displayed in the diagnostic image 2702.

In addition, even when the user input is not present, the processor 420 may move a contour line of the lesion area 2510 included in the ultrasonic image (e.g., 2501) in a clockwise orientation or a counterclockwise orientation and control to generate and display the diagnostic image (e.g., 2502) in which at least one of an area corresponding to a position at which the contour line is moved and information (e.g., 2551) on a feature appearing in the area is displayed.

In addition, the processor 420 may divide the contour line of the lesion area 2510 included in the ultrasonic image (e.g., 2501) into a plurality of sections and control to generate and display a diagnostic image in which at least one of an area corresponding to the divided section and information on a feature appearing in the area. In addition, the plurality of sections may be displayed to be distinguished from each other using at least one among different colors, marks, symbols, transparency, echoes, types of dotted lines, and thicknesses of the dotted lines.

Figure 28:
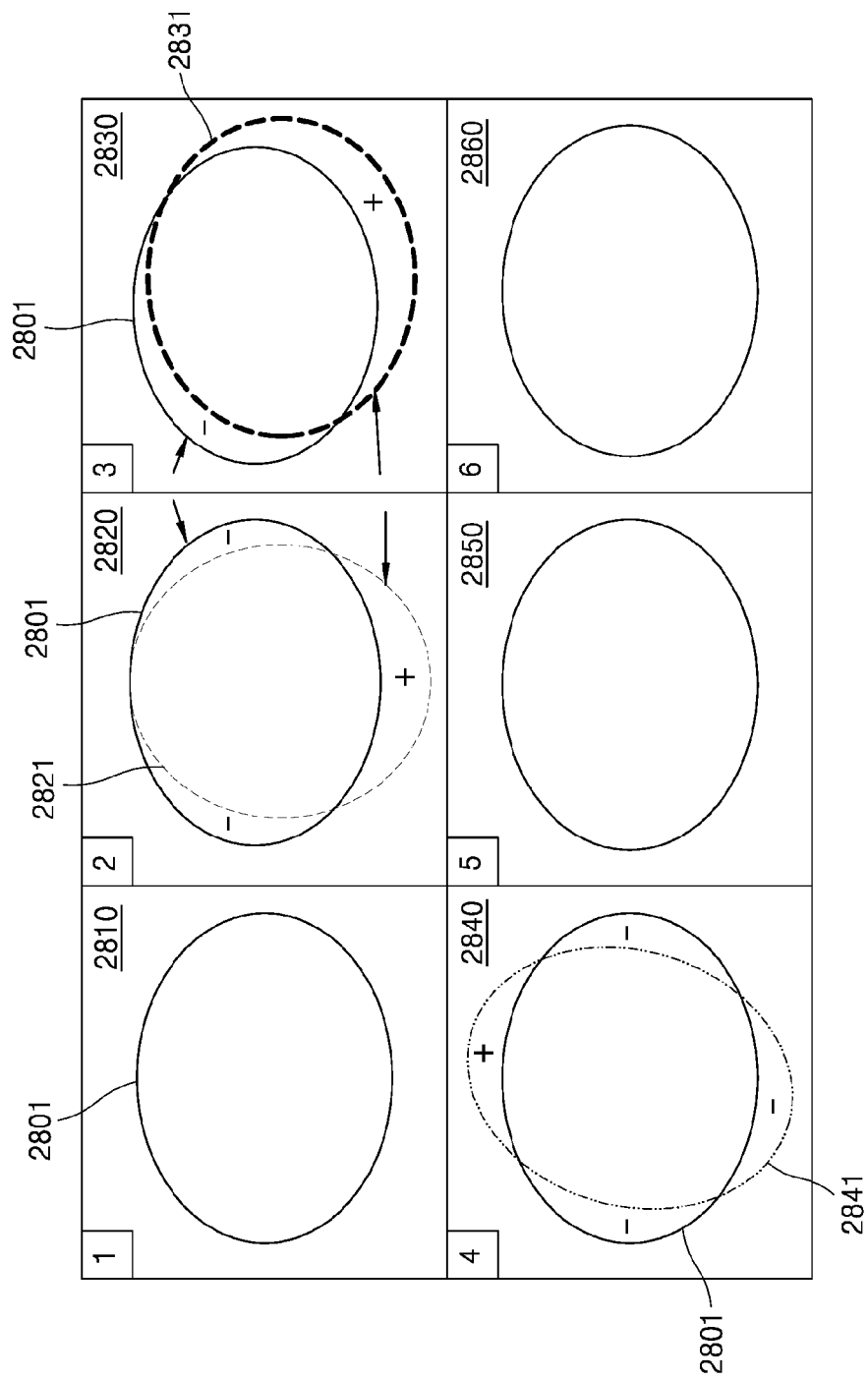
FIG. 28 is a diagram illustrating a user interface screen including a plurality of diagnostic images.

FIG. 28 is a diagram illustrating a user interface screen including a plurality of diagnostic images.

In the disclosed embodiment, in order to identify the lesion area, the processor 420 may extract the contour of the lesion using at least one of a CAD technology and an AI technology. In addition, when a plurality of extracted contours of the lesion are present, the processor 420 may control to generate and display a user interface screen including a plurality of ultrasonic images in which the plurality of extracted contours of the lesion are displayed.

In addition, when a plurality of extracted contours of the lesion are present and each of the plurality of extracted contours corresponds to a different diagnostic result, the processor 420 may control to generate and display a user interface screen including a plurality of ultrasonic images in which the plurality of extracted contours of the lesion are displayed.

Referring to FIG. 28, a user interface screen 2800 may include a plurality of ultrasonic images 2810, 2820, 2830, 2840, 2850, and 2860. Here, each of the plurality of ultrasonic images 2810, 2820, 2830, 2840, 2850, and 2860 included in the user interface screen 2800 may be an ultrasonic image in which a different contour is displayed.

In addition, each of the plurality of ultrasonic images 2810, 2820, 2830, 2840, 2850, and 2860 may be disposed in the order of accuracy of an extracted contour. For example, the ultrasonic image 2810 in which a contour 2801 having the highest contour accuracy is displayed may be disposed at a first position, and the ultrasonic image 2820 in which a contour 2821 having second highest contour accuracy is displayed may be disposed at a second position. In addition, the ultrasonic image 2830 in which a contour 2831 having third highest contour accuracy is displayed may be disposed at a third position, and the ultrasonic image 2840 in which a contour 2841 having fourth highest contour accuracy is displayed may be disposed at a fourth position.

In addition, in each of the plurality of ultrasonic images 2820, 2830, 2840, 2850, and 2860, the contour 2801 having the highest contour accuracy may be illustrated as a comparison target.

In addition, a diagnostic result (not shown in FIG. 28) derived on the basis of the extracted contour may be displayed in each of the plurality of ultrasonic images 2810, 2820, 2830, 2840, 2850, and 2860.

In addition, when each of the plurality of ultrasonic images 2810, 2820, 2830, 2840, 2850, and 2860 is selected on the user interface screen 2800, a diagnostic image including diagnostic information corresponding to the diagnostic result may be enlarged and displayed.

Figure 29:
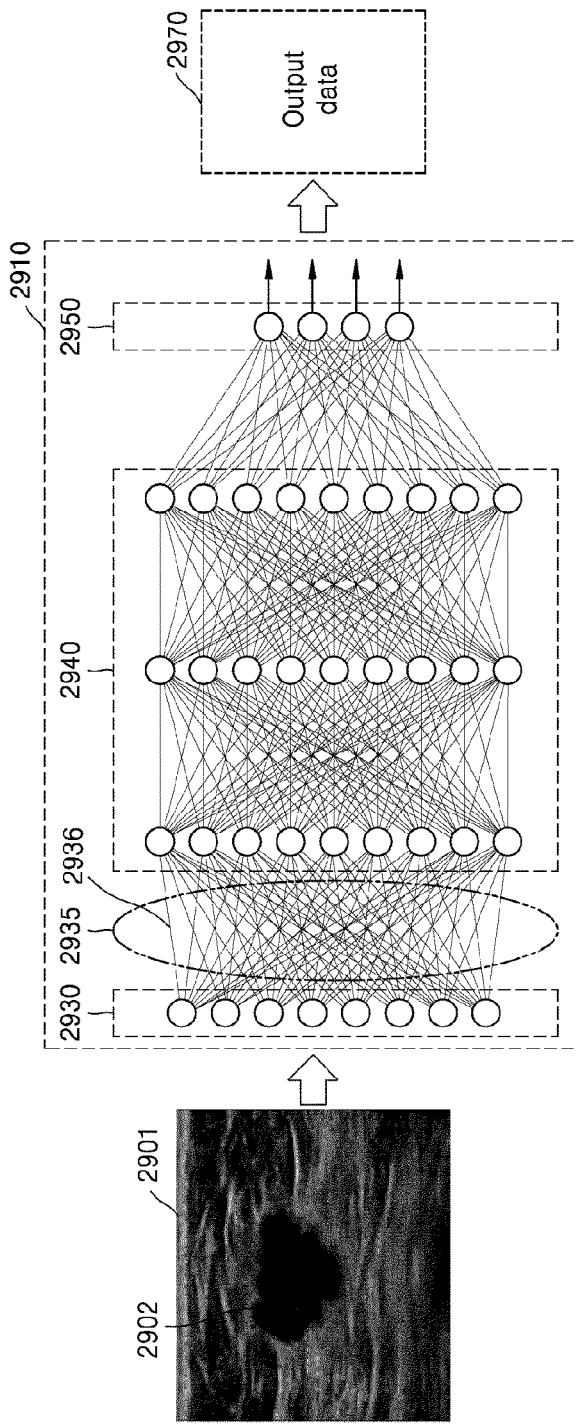
FIG. 29 is a diagram for describing a neural network used for acquiring an analysis result of an ultrasonic image.

FIG. 29 is a diagram for describing a neural network used for acquiring an analysis result of an ultrasonic image.

In the disclosed embodiment, the processor 420 may analyze a lesion using at least one of a CAD technology and an AI technology and acquire at least one among a lesion area, a diagnostic result, and diagnostic information corresponding to the diagnostic result.

Hereinafter, an operation of acquiring at least one among the lesion area, the diagnostic result, and the diagnostic information corresponding to the diagnostic result using an AI technology will be described.

The AI technology is a technology for obtaining a desired result by performing an operation through a neural network to analyze an input image or input data. Here, the neural network may train training data (e.g., a plurality of different ultrasonic images) to optimize and set weight values in the neural network. Then, the neural network learns the input data by itself through a neural network having the optimized weight value, thereby outputting a desired result.

Specifically, the neural network may be a DNN. In addition, an operation of the DNN may include an operation of a CNN. Specifically, a data recognition model may be implemented through an exemplified neural network, and the implemented data recognition model may be trained using training data. In addition, data to be input, for example, an ultrasonic image including a lesion area, may be analyzed or classified using the learned data recognition model, and a specific area (e.g., a contour area of the lesion) or a specific area image (e.g., an image corresponding to a partial area that is the basis of deriving a diagnostic result, as in a first area), which is included in the ultrasonic image, may be analyzed and/or classified.

In the embodiment of the present disclosure, the processor 420 may perform an operation through a neural network to acquire at least one among the lesion area, the diagnostic result, and the diagnostic information corresponding to the diagnostic result from the ultrasonic image.

Alternatively, the above-described operation through the neural network may be performed by the image processing unit 450.

Alternatively, the above-described operation through the neural network may performed through an external server (not shown), and the operation result through the neural network (e.g., at least one among the lesion area, the diagnostic result, and the diagnostic information corresponding to the diagnostic result) may be received through the communication unit 470.

The processor 420 may perform an operation through a neural network including an input layer, a hidden layer, and an output layer, for example, a DNN 2920. In FIG. 9, a case in which a hidden layer included in a neural network is formed as a DNN formed of multiple stages is illustrated as an example.

Referring to FIG. 29, the DNN 2920 includes an input layer 2930, a hidden layer 2940, and an output layer 2950. In FIG. 29, the DNN 2920 which analyzes information included in an ultrasonic image that is input data and outputs desired output data 2970 is illustrated as an example. Here, the output data 2970 may include at least one among a lesion area, a diagnostic result, and diagnostic information corresponding to the diagnostic result.

A plurality of layers forming the DNN 2920 may include a plurality of nodes (e.g., 2931) for receiving data. In addition, as shown in the drawing, two adjacent layers are connected by a plurality of edges (e.g., 2936). Each node has a corresponding weight value. Accordingly, the DNN 2920 may acquire output data by calculating an input signal and a weight value, for example, on the basis of a value obtained by performing a convolution operation.

Here, the DNN 2920 may be formed as a CNN neural network which performs a CNN operation.

Referring to the example shown in FIG. 29, the input layer 2930 receives an ultrasonic image 2910 including a lesion area 2902.

In FIG. 29, a case in which the hidden layer 2940 is formed of three-stage layers is illustrated as an example. A depth of the hidden layer 2940 may be varied according to an $n^{th}$ order specification and/or design specification of a used neural network.

Referring to FIG. 29, the DNN 2920 includes a first layer Layer 1 formed between the input layer 2930 and a first hidden layer HIDDEN LAYER1, a second layer Layer 2 formed between the first hidden layer HIDDEN LAYER1 and a second hidden layer HIDDEN LAYER2, a third layer Layer 3 formed between the second hidden layer HIDDEN LAYER2 and a third hidden layer HIDDEN LAYER3, and a fourth layer Layer 4 formed between the third hidden layer HIDDEN LAYER3 and the output layer 2970.

A plurality of nodes included in the input layer 2930 of the DNN 2920 receive a plurality of pieces of data corresponding to the ultrasonic image 2910. Here, the plurality of pieces of data may be a plurality of partial images generated by performing a filter process to divide the ultrasonic image 2910.

In addition, the output layer 2950 may output the output data 2970 acquired as the analysis result of the ultrasonic image 2910 through operations in the plurality of layers included in the hidden layer 2940.

Specifically, when the DNN 2920 is formed of a CNN and when a correlation between information included in an image is local, the CNN may introduce a concept of a filter illuminating only a specific area and perform a convolution operation on pieces of information in the filter, thereby precisely extracting information on a feature of an image in the filter.

Specifically, a convolution layer and a pooling layer are alternately disposed in the hidden layer 2940 existing in the CNN-based neural network 2920, and a depth of a filter of each layer is increased from left to right. In addition, the final stage of the CNN-based neural network 2920 may be formed as a fully connected layer. Here, the convolution layer is a layer of data generated according to a convolution operation, and the pooling layer is a layer for reducing the number of pieces of data or size of data through an operation such as subsampling or pooling. Pieces of data (e.g., a feature map) indicating a feature of an input image is generated by passing through the convolution layer and the pooling layer. Specifically, image features of the ultrasonic image 2910 are generated through the operation of the hidden layer 2940, and a lesion area, a diagnostic result with respect to the lesion, and diagnostic information corresponding to the diagnostic result may be acquired on the basis of the image features.

In addition, when the pieces of data generated by passing through the convolutional layer and the pooling layer are processed through the hidden layer formed as a fully connected layer, the desired output data 2970 may be output.

In addition, in order to increase accuracy of the output data output through the DNN 2920, training may be performed in an orientation from the output layer 2950 to the input layer 2930, and in order to increase accuracy of the output data, weight values of nodes (e.g., 2931) forming the DNN 2920 may be corrected. Therefore, before the ultrasonic image 2910 is input, the DNN 2920 may learn a plurality of ultrasonic images including a plurality of different lesions to correct a weight value of each node in an orientation of a lesion area included in the ultrasonic image or in an orientation in which a diagnostic result is accurately detected.

In addition, the DNN 2920 may perform an operation through the neural network to acquire a criterion for detecting the diagnostic result. For example, criteria indicating features of a malignant lesion or criteria indicating feature values of a benign lesion may be acquired.

FIG. 30 is a flowchart illustrating a method of displaying an ultrasonic image according to an embodiment. A method 3000 of displaying an ultrasonic image according to the disclosed embodiment may be performed through the ultrasound diagnosis device 100, 400, or 500 according to the disclosed embodiments described with reference to FIGS. 1 to 29. Therefore, each operation of the method 3000 of displaying an ultrasonic image may be performed through each configuration of the ultrasound diagnosis device 100, 400, or 500, and the method 3000 of displaying an ultrasonic image may include the same configurational features as in the above-described ultrasound diagnosis device 100, 400, or 500. That is, FIG. 30 may be a diagram illustrating operations performed by the ultrasound diagnosis device 100, 400 or 500 according to the disclosed embodiments. Therefore, in describing the method 3000 of displaying an ultrasonic image, descriptions overlapping those of FIGS. 1 to 29 will be omitted herein.

The method 3000 of displaying an ultrasonic image identifies a lesion area included in an ultrasonic image (S3010). Operation S3010 may be performed by the processor 420.

The lesion area identified in operation S3010 is diagnosed to acquire a diagnostic result (S3020). Operation S3020 may be performed by the processor 420.

Then, in the lesion area, a first area, which is at least one area that is the basis of diagnosing a lesion, is displayed in the lesion area of the ultrasonic image to generate a diagnostic image (S3030). Operation S3030 may be performed by the processor 420.

Then, a user interface screen including the diagnostic image and the diagnostic result is displayed (S3040). Operation S3040 may be performed by the processor 420.

FIG. 31 is a diagram illustrating an actual implementation example of the user interface screen according to the embodiment.

Figure 32:
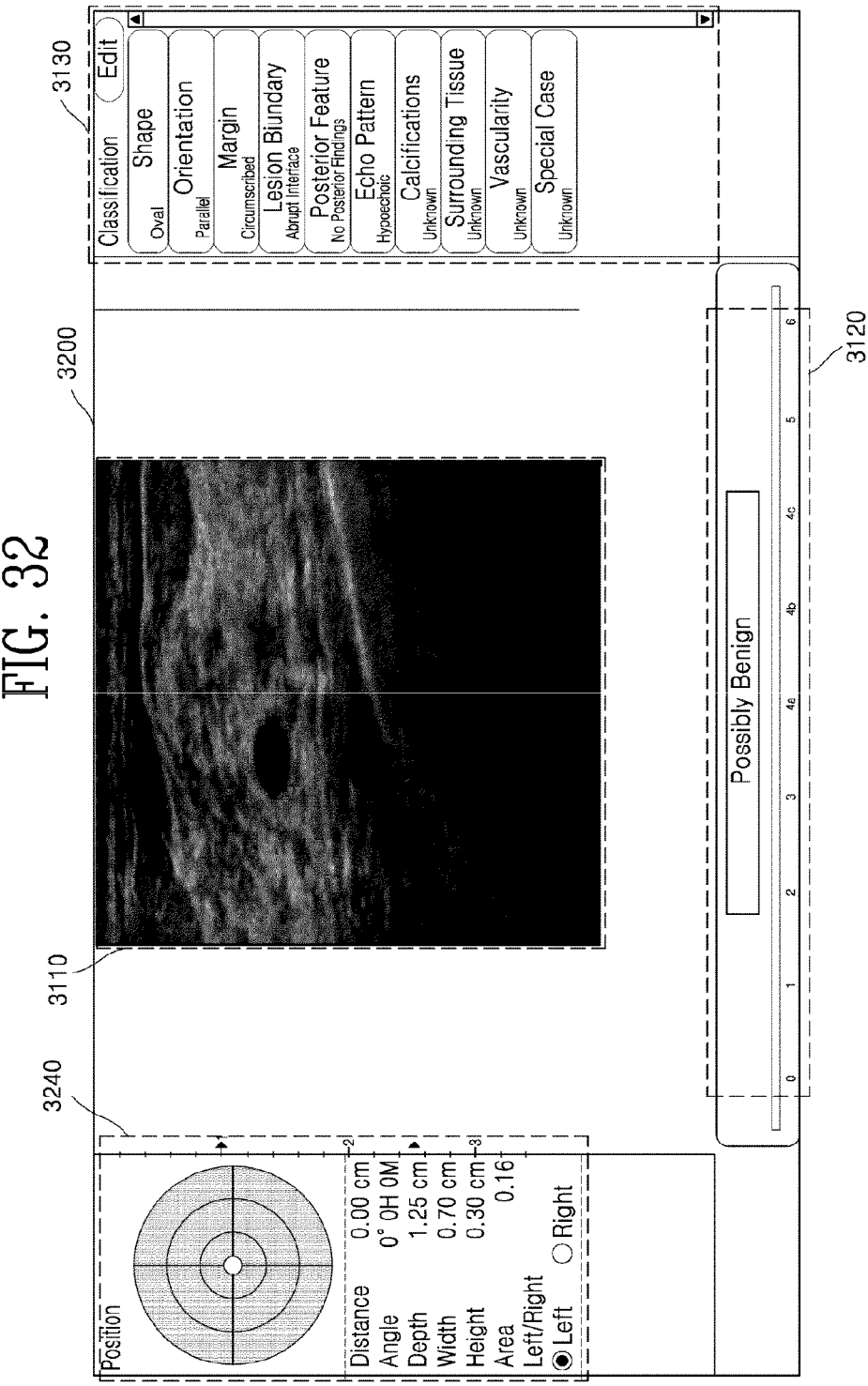
FIG. 32 is another diagram illustrating an actual implementation example of the user interface screen according to the embodiment.

FIG. 32 is another diagram illustrating an actual implementation example of the user interface screen according to the embodiment.

Specifically, in FIGS. 31 and 32, an actual user interface screen output from the ultrasound diagnosis device implemented according to the disclosed embodiments is illustrated.

Referring to FIG. 31, a user interface screen 3100 may include a diagnostic image 3110 generated by marking an extracted contour area in an ultrasonic image, a diagnostic result 3120, and a list 3130 indicating features of a lesion area. Here, the diagnostic image 3110, the diagnostic result 3120, and the list 3130 indicating the features of the lesion area identically correspond to the diagnostic image 1310, the diagnostic result 1330, and the list 1302 indicating the features of the lesion area shown in FIG. 13, respectively, and thus detailed descriptions thereof will be omitted herein.

In the disclosed embodiment, due to selection of at least one item in the list 3130 or a setting of the processor 420, the first area may be displayed in the diagnostic image 3110.

Referring to FIG. 32, when compared to the user interface screen 3200, a user interface screen 3200 may further include ultrasound scan information 3240 with respect to a patient or an object.

Meanwhile, the disclosed embodiments may be implemented in the form of a computer-readable recording medium storing commands executable by a computer and data. The command may be stored in the form of a program code, and when the command is executed by a processor, a predetermined program module may be generated to perform a predetermined operation. In addition, when the command is executed by a processor, the command may perform predetermined operations of the disclosed embodiments.

The computer-readable medium may include program instructions, data files, data structures, and the like in alone or a combination thereof. The program command recorded in the computer-readable medium may be specially designed and configured for the embodiment or may be available to those skilled in the computer software. Examples of the computer-readable recording media include magnetic media such as a hard disk, a floppy disk, and a magnetic tape, optical recording media such as a compact disc read only memory (CD-ROM) and a digital versatile disc (DVD), a magneto-optical medium such as a floptical disk, and hardware devices specifically configured to store and execute program commands, such as a ROM, a RAM, a flash memory, and the like. Examples of the program commands include machine language codes generated by a compiler as well as high-level language codes which are executable by a computer using an interpreter or the like.

In addition, the method of displaying an ultrasonic image according to the above-described embodiment may be implemented as a computer program product including a recording medium in which a program is stored, wherein the program performs an operation of acquiring a sentence composed of multiple languages; and an operation of acquiring vector values corresponding to words included in the multilingual sentence using a multilingual translation model, converting the acquired vector values into vector values corresponding to a target language, and acquiring a sentence composed of the target language on the basis of the converted vector values.

The invention claimed is:

1. A method of displaying an ultrasonic image, comprising:
   identifying a lesion area included in the ultrasonic image;
   diagnosing the lesion area to acquire a diagnostic result;
   generating a diagnostic image including a first area in the lesion area, which is at least one area that is the basis of diagnosing the lesion, in the ultrasonic image;
   displaying a user interface screen including the diagnostic image and the diagnostic result; and
   displaying the diagnostic image displaying a second area in the lesion area, which is at least one area indicating a feature of the lesion that changes the diagnostic result when the feature of the lesion is changed,
   wherein the displaying of the diagnostic image displaying the second area in the lesion area, includes displaying visual information indicating that the diagnostic result will be changed when the feature of the lesion in the second area is changed.

2. The method of claim 1, wherein the first area is an area indicating at least one feature among a plurality of features of the lesion in lesion area.

3. The method of claim 1, wherein the first area is an area that is the basis of determining at least one feature among a shape of the lesion, an orientation of the lesion, a margin of the lesion, an echo with respect to the lesion area, and a posterior of the lesion area.

4. The method of claim 1, wherein the diagnostic result includes information indicating whether the lesion is benign or malignant.

5. The method of claim 1, wherein the first area includes a plurality of areas indicating each of a plurality of features, wherein the generating of the diagnostic image includes:
displaying the plurality of areas in the lesion area using at least one among different colors, marks, symbols, transparency, echoes, types of dotted line, and thicknesses of the dotted lines, thereby distinguishing different features from each other among the plurality of features; and
the plurality of features include at least one among a shape of the lesion, an orientation of the lesion, a margin form of the lesion, an echo with respect to the lesion area, and a posterior feature of the lesion area that are the basis of diagnosing the lesion.

6. The method of claim 1, wherein the generating of the diagnostic image further includes displaying the first area to be distinguished from the second area in the diagnostic image.

7. The method of claim 1, wherein the displaying of the user interface screen includes displaying the user interface screen including a list including a plurality of items corresponding to a plurality of features indicating at least one of the diagnostic image, the diagnostic result, or the lesion.

8. The method of claim 7, further comprises:
in response to a user input for selecting any one among the plurality of items, displaying at least one partial area indicating a feature corresponding to a selected item in the diagnostic image.

9. The method of claim 7, wherein the displaying of the user interface screen further includes, in accordance that when a first feature is changed and the diagnostic result is changed, displaying an item included in the list corresponding to the first feature to be distinguished from other items.

10. The method of claim 1, wherein the generating of the diagnostic image includes generating the diagnostic image including diagnostic information, which is information about a feature of the lesion area appearing in the first area.

11. The method of claim 10, wherein the generating of the diagnostic image including the diagnostic information includes analyzing the ultrasonic image using at least one of a computer aided detection & diagnosis (CAD) technology and an artificial intelligence (AI) technology and acquiring at least one among the lesion area, the diagnostic result, and diagnostic information corresponding to the diagnostic result.

12. An ultrasound diagnosis device comprising:
a display;
a memory configured to store at least one instruction; and
a processor configured to execute at least one of the at least one instruction to:
identify a lesion area included in an ultrasonic image, diagnose the lesion area to acquire a diagnostic result,
generate a diagnostic image including a first area, which is at least one area that is the basis of diagnosing a lesion in the lesion area, in the ultrasonic image,
control the display to display a user interface screen including the diagnostic image and the diagnostic result, and
control the display to display the diagnostic image displaying a second area in the lesion area, which is at least one area indicating a feature of the lesion that changes the diagnostic result when the feature of the lesion is changed,
wherein the displaying of the diagnostic image displaying the second area in the lesion area, includes displaying visual information indicating that the diagnostic result will be changed when the feature of the lesion in the second area is changed.

13. A non-transitory computer-readable recording medium, in which a computer program including commands executable by a computer is stored, when the computer program is executed by a computer, causing the computer to perform:
identifying a lesion area included in an ultrasonic image;
diagnosing the lesion area to acquire a diagnostic result;
generating a diagnostic image including a first area in the lesion area, which is at least one area that is the basis of diagnosing the lesion, in the ultrasonic image; displaying a user interface screen including the diagnostic image and the diagnostic result; and
displaying the diagnostic image displaying a second area in the lesion area, which is at least one area indicating a feature of the lesion that changes the diagnostic result when the feature of the lesion is changed,
wherein the displaying of the diagnostic image displaying the second area in the lesion area, includes displaying visual information indicating that the diagnostic result will be changed when the feature of the lesion in the second area is changed.

* * * * *